(12) United States Patent
Yan et al.

(10) Patent No.: US 10,960,078 B2
(45) Date of Patent: Mar. 30, 2021

(54) AMPHIPHILIC DRUG-DRUG CONJUGATES FOR CANCER THERAPY, COMPOSITIONS AND METHODS OF PREPARATION AND USES THEREOF

(71) Applicant: Shanghai Jiao Tong University, Shanghai (CN)

(72) Inventors: Deyue Yan, Shanghai (CN); Ping Huang, Shanghai (CN); Xinyuan Zhu, Shanghai (CN); Wei Huang, Shanghai (CN); Yongfeng Zhou, Shanghai (CN)

(73) Assignee: Shanghai Jiao Tong University, Shanghai (CN)

( * ) Notice: Subject to any disclaimer, the term of this patent is extended or adjusted under 35 U.S.C. 154(b) by 0 days.

(21) Appl. No.: 16/587,295

(22) Filed: Sep. 30, 2019

(65) Prior Publication Data

US 2020/0023066 A1 Jan. 23, 2020

Related U.S. Application Data

(63) Continuation of application No. 15/352,256, filed on Nov. 15, 2016, now Pat. No. 10,463,743, which is a continuation of application No. 14/203,596, filed on Mar. 11, 2014, now Pat. No. 9,533,054.

(60) Provisional application No. 61/786,734, filed on Mar. 15, 2013, provisional application No. 61/775,724, filed on Mar. 11, 2013.

(51) Int. Cl.
| | |
|---|---|
| *A61K 31/7068* | (2006.01) |
| *A61K 31/7072* | (2006.01) |
| *A61K 31/352* | (2006.01) |
| *A61K 31/131* | (2006.01) |
| *A61K 31/4184* | (2006.01) |
| *A61K 31/519* | (2006.01) |
| *A61P 35/00* | (2006.01) |
| *A61K 47/55* | (2017.01) |
| *C07H 19/073* | (2006.01) |
| *C07H 19/067* | (2006.01) |
| *C07H 19/06* | (2006.01) |
| *A61K 47/69* | (2017.01) |
| *A61K 47/54* | (2017.01) |
| *A61K 31/196* | (2006.01) |
| *A61K 31/365* | (2006.01) |
| *A61K 31/4745* | (2006.01) |
| *A61K 9/14* | (2006.01) |

(52) U.S. Cl.
CPC .......... *A61K 47/55* (2017.08); *A61K 31/131* (2013.01); *A61K 31/196* (2013.01); *A61K 31/352* (2013.01); *A61K 31/365* (2013.01); *A61K 31/4184* (2013.01); *A61K 31/4745* (2013.01); *A61K 31/519* (2013.01); *A61K 31/7068* (2013.01); *A61K 31/7072* (2013.01); *A61K 47/549* (2017.08); *A61K 47/6929* (2017.08); *A61P 35/00* (2018.01); *C07H 19/06* (2013.01); *C07H 19/067* (2013.01); *C07H 19/073* (2013.01); *A61K 9/14* (2013.01)

(58) Field of Classification Search
None
See application file for complete search history.

(56) References Cited

U.S. PATENT DOCUMENTS 10,463,743 B2 * 11/2019 Yan ............... A61K 47/6929
2013/0122056 A1 * 5/2013 Zhang ............ A61K 31/7048
424/400

OTHER PUBLICATIONS

Wang et al., "Heparin-Paclitaxel Conjugates as Drug Delivery System: Synthesis, Self-Assembly Drug Release, and Antitumor Activity" Bioconjugate Chemistry vol. 20 pp. 2214-2221 (Year: 2009).*

* cited by examiner

*Primary Examiner* — Eric Olson
(74) *Attorney, Agent, or Firm* — Milstein Zhang & Wu LLC

(57) ABSTRACT

The invention provides novel amphiphilic drug-drug conjugates useful as cancer therapeutics, and compositions and methods thereof.

7 Claims, 26 Drawing Sheets

AMPHIPHILIC DRUG-DRUG CONJUGATES FOR CANCER THERAPY, COMPOSITIONS AND METHODS OF PREPARATION AND USES THEREOF

PRIORITY CLAIMS AND RELATED PATENT APPLICATIONS

This application is a continuation of and claims the benefit to U.S. patent application Ser. No. 15/352,256, filed Nov. 16, 2016, which is a continuation of and claims the benefit of priority to U.S. patent application Ser. No. 14/203,596, filed Mar. 11, 2014, now U.S. Pat. No. 9,533,054, which claims the benefit of priority to U.S. Provisional Application Ser. No. 61/775,724, filed on Mar. 11, 2013, and Ser. No. 61/786,734, filed on Mar. 15, 2013, the entire content of each of which is incorporated herein by reference in its entirety for all purposes.

TECHNICAL FIELD OF THE INVENTION

The invention generally relates to novel cancer therapeutics and related compositions and methods. More particularly, the invention relates to novel amphiphilic drug-drug conjugates useful as cancer therapeutics, and compositions and methods thereof.

BACKGROUND OF THE INVENTION

Cancer is characterized by rapidly-proliferating cell growth in the body. Cancer is often able to invade other tissues from its original location and, in a process called metastasis, spread to other parts of the body through blood and lymphatics. Despite decades of intensive scientific and clinical research, cancer remains a major health threat to the public. There are many types of cancer, which may be classified in pathology and clinical diagnosis into carcinoma, sarcoma, leukemia, lymphoma and myeloma, and malignant tumors of the central nervous system. While significant advancements have been made in cancer prevention and treatment, cancer remains a challenging disease to both the patient and the healthcare provider. Cancer is the leading disease of mortality in all countries of the world. (Ferlay, et al. 2010 *Int. J. Cancer* 127, 2893-2917.)

Currently, four standard approaches have been proposed for cancer treatment: surgery, chemotherapy, radiation therapy, immunotherapy and biologic therapy. Among various cancer treatments, chemotherapy is an indispensable choice for most cancer cases because of its high efficiency. Unfortunately, due to the small molecular size of free anticancer drugs, conventional chemotherapy suffers from several limitations including poor bioavailability, rapid blood/renal clearance, non-specific selectivity, low accumulation in tumors, severe MDR, and adverse side effects for healthy tissues. To address these limitations, some nano-vehicles including water-soluble polymers, liposomes, vesicles, polymeric nanoparticles and inorganic materials have been used as drug carriers. (Park, et al. 2008 *Prog. Polym. Sci.* 33, 113-137; Hubbell, et al. 2012 *Science* 337, 303-305; Tong, et al. 2007 Polym. Rev. 47, 345-381; Riehemann, et al. 2009 *Angew. Chem., Int. Ed.* 48, 872-897; Fox, et al. 2009 *Acc. Chem. Res.* 42, 1141-1151; Lutz, et al. 2008 *Prog. Polym. Sci.* 33, 1-39; Kiick, et al. 2007 *Science* 317, 1182-1183; Lee, et al. 2005 *Nat. Biotechnol.* 23, 1517-1526; Zhou, et al. 2010 *Adv. Mater.* 22, 4567-4590; Liu, et al. 2010 *Biomaterials* 31, 5643-5651; Lee, et al. 2007 *J. Am. Chem. Soc.* 129, 15096-15097; Volodkin, et al. 2009 *Angew. Chem., Int. Ed.* 48, 1807-1809; Linderoth, et al. 2009 *J. Am. Chem. Soc.* 131, 12193-12200; Holme, et al. 2012 *Nat. Nanotech.* 7, 536-543; Song, et al. 2012 *J. Am. Chem. Soc.* 134, 13458-13469; Kataoka, et al. 2001 *Adv. Drug Deliv. Rev.* 47, 113-131; Griset, et al. 2009 *J. Am. Chem. Soc.* 131, 2469-2471; Tong, et al. 2008 *Angew. Chem., Int. Ed.* 47, 4830-4834; Chen, et al. 2008 *J. Am. Chem. Soc.* 130, 16778-16785; Kim, et al. 2010 *Nat. Nanotech.* 5, 465-472.)

With the help of these nano-vehicles, drugs can be delivered to the action sites of body via physical entrapment or chemical conjugation, demonstrating better therapeutic efficacy against tumors and fewer side effects over free drugs. (Wang, et al. 2011 *Biomacromolecules* 12, 1370-1379; Shen, et al. 2010 *J. Am. Chem. Soc.* 132, 4259-4265; Li, et al. 2011 *Biomacromolecules* 12, 2016-2026; Du, et al. 2011 *J. Am. Chem. Soc.* 133, 17560-17563; Singer, et al. 2001 *J. Control. Release* 74, 243-247; Paranjpe, et al. 2005 *Anticancer Drugs* 16, 763-775; Khandare, et al. 2006 *J. Pharmacol. Exp. Ther.* 317, 929-937.) However, almost all carriers have no therapeutic efficacy by themselves. Even worse, a lot of carriers with low drug loading capacity may arouse side-effects to kidneys and other organs in the course of degradation, metabolism and excretion, such as high toxicity and serious inflammation. (Greenwald, et al. 2003 *Adv. Drug Deliv. Rev.* 55, 217-250; Yu, et al. 2005 *J. Control. Release* 110, 90-102.)

There remains an ongoing unmet need for novel and effective antitumor therapeutics.

SUMMARY OF THE INVENTION

The invention provides a unique approach to drug delivery in cancer therapy: amphiphilic drug-drug conjugate (ADDC), which can assist in overcoming these barriers. To demonstrate the unique approach, an exemplary ADDC was synthesized from hydrophilic anticancer drug irinotecan (Ir) and hydrophobic anticancer drug chlorambucil (Cb). These two drugs were linked together through an ester bond. The amphiphilic Ir-Cb ADDC self-assembled into nanoparticles in water, exhibiting longer blood circulation half-life compared with that of free drugs. The Ir-Cb ADDC could be accumulated in tumor tissues via the enhanced permeability and retention (EPR) effect, which promoted cellular uptake of the ADDC. Benefiting from the nano-scale characteristics of Ir-Cb ADDC nanoparticles, the multidrug resistance (MDR) of tumor cells can be overcome efficiently. After cellular internalization, the ester bond between Ir and Cb was hydrolyzed within the acidic environment of lysosome, releasing both hydrophilic and hydrophobic drugs. The synergistic action of two released drugs showed efficient proliferation inhibition against tumor cells.

In one aspect, the invention generally relates to an amphiphilic compound comprising a hydrophilic moiety and a hydrophobic moiety conjugated via a linkage capable of cleavage under an acidic condition, wherein each of the hydrophilic moiety and the hydrophobic moiety is independently an antitumor agent.

In another aspect, the invention generally relates to a pharmaceutical composition comprising an amphiphilic compound disclosed herein, or a pharmaceutically acceptable ester thereof, in an amount effective in the treatment of cancer in a mammal, including a human.

In yet another aspect, the invention generally relates to a method of treating cancer, comprising administering to a subject in need thereof a therapeutically effective amount of a pharmaceutical composition comprising an amphiphilic compound disclosed herein, or a pharmaceutically acceptable ester thereof, effective in the treatment of cancer in a mammal, including a human.

In yet another aspect, the invention generally relates to a nanoparticle comprising an amphiphilic compound disclosed herein.

In yet another aspect, the invention generally relates to a pharmaceutical composition comprising a nanoparticle disclosed herein in an amount effective in the treatment of cancer in a mammal, including a human.

In yet another aspect, the invention generally relates to a method of treating cancer, comprising administering to a subject in need thereof a therapeutically effective amount of a pharmaceutical composition comprising a nanoparticle disclosed herein, effective in the treatment of cancer in a mammal, including a human.

DETAILED DESCRIPTION OF THE INVENTION

The invention provides novel amphiphilic drug-drug conjugates useful as cancer therapeutics, and compositions and methods thereof.

It can be imagined that if the anticancer drugs could exhibit nano-scale characteristics by themselves without the help of nano-vehicles, a promising drug delivery system integrating both advantages of free drugs and nanocarriers could be expected. Aiming at this goal, a new ADDC drug self-delivered system has been developed for cancer therapy.

Figure 1:
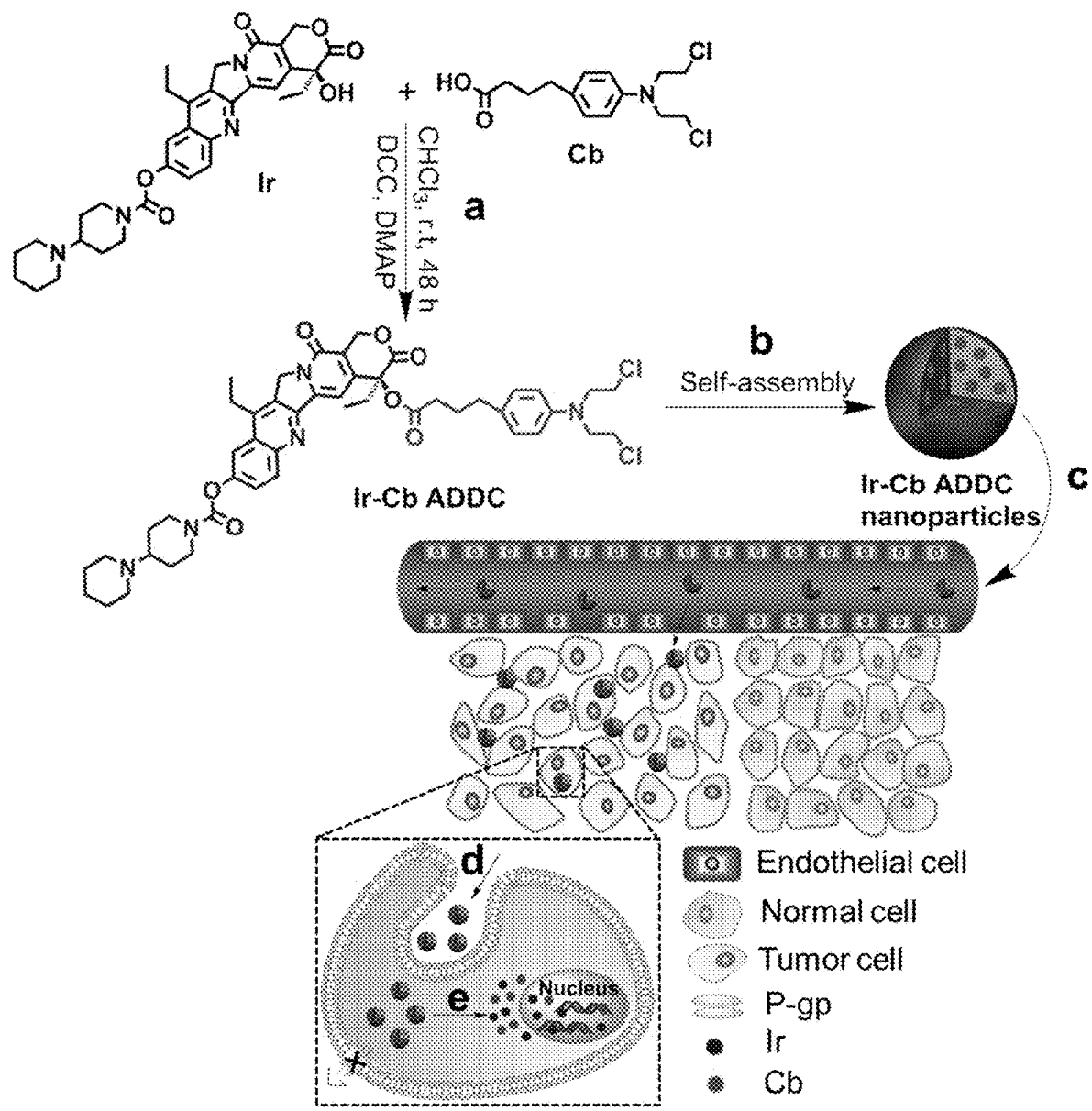
FIG. 1. Schematic diagram of amphiphilic drug-drug conjugate (ADDC) from fabrication, self-assembly to self-delivery. a, Scheme for the synthesis of Ir-Cb ADDC through esterification in DCC/DMAP-catalyzed system. b, The Ir-Cb ADDC self-assembles into nanoparticles in water. c, Passive tumor targeting is achieved by the advantage of EPR effect, which facilitates the Ir-Cb ADDC nanoparticles to access tumors by way of their leaky vasculature. d, The Ir-Cb ADDC nanoparticles enter tumor cells by endocytosis. e, Ir and Cb are released by the cleavage of the ester bond in tumor cells and then diffuse into nucleus.
Figure 2:
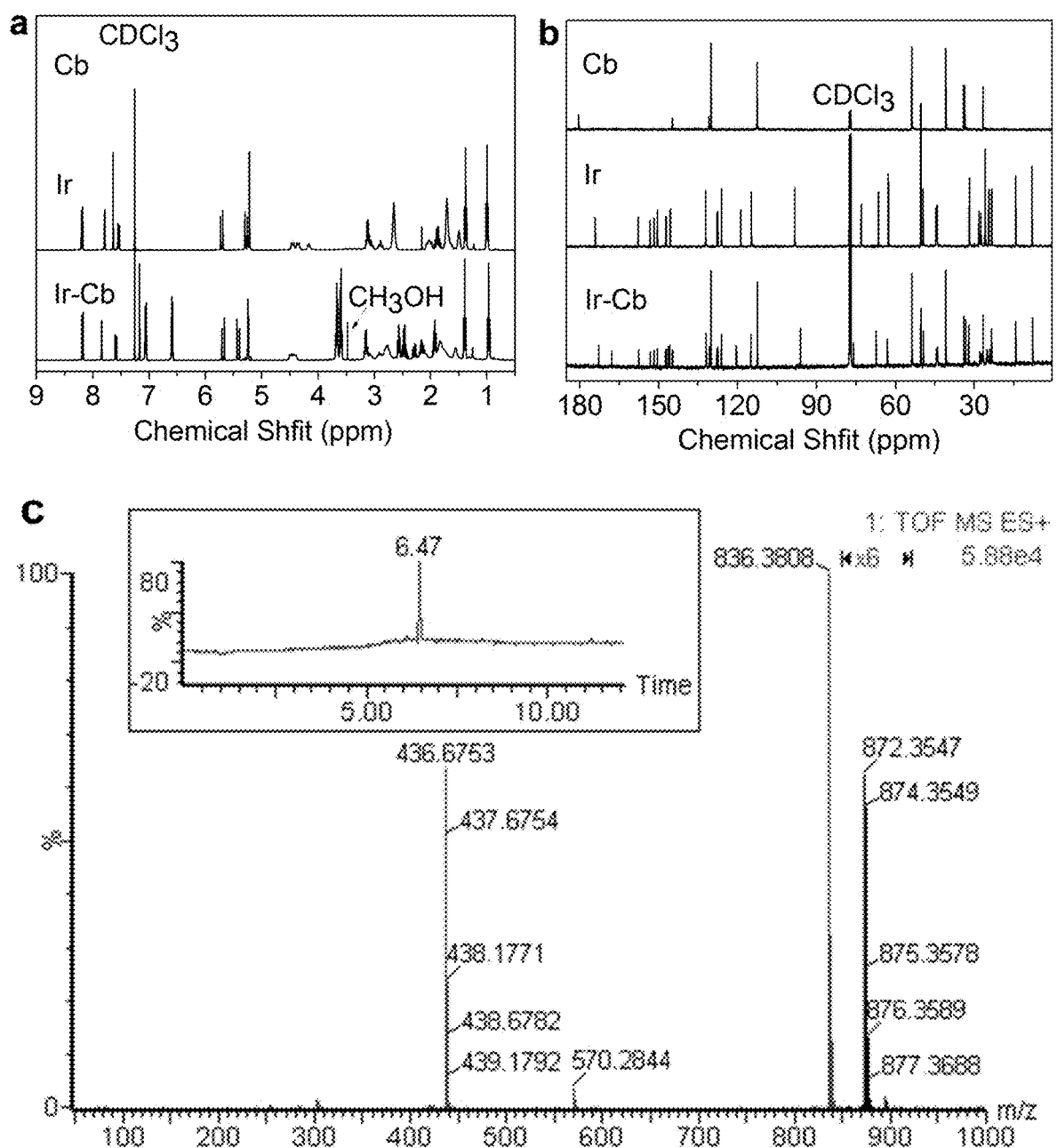
FIG. 2. a,b, $^1$H NMR (a) and $^{13}$C NMR (b) spectra of Cb, Ir and Ir-Cb ADDC in CDCl$_3$, c, Mass spectrum of Ir-Cb ADDC (ESI-MS m/z (M+H$^+$) calcd 872.3557, found 872.3547 (M+H$^+$)). Inset: LC profile of Ir-Cb ADDC. Retention time ($t_R$) is 6.47 min.
Figure 3:
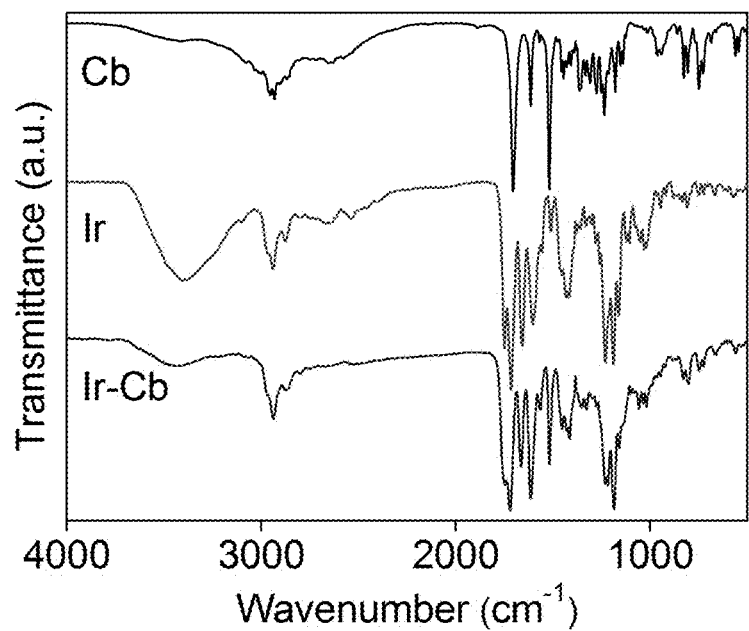
FIG. 3. FTIR spectra of Cb, Ir and Ir-Cb conjugate.
Figure 4:
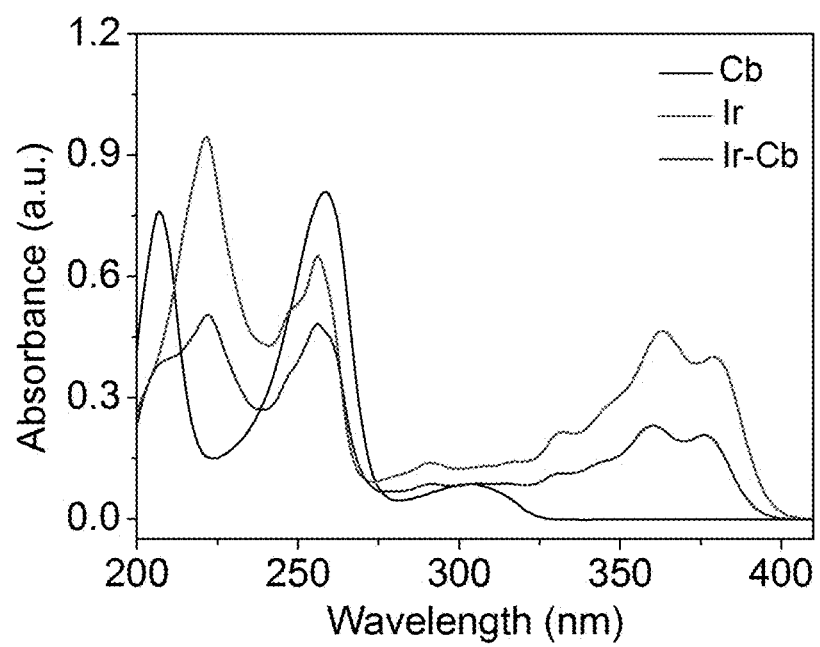
FIG. 4. UV/Vis spectra of Cb, Ir and Ir-Cb conjugate in acetonitrile.

Described herein is the novel ADDC strategy in FIG. 1. The conjugate consists of a water-soluble anticancer drug Ir and a water-insoluble anticancer drug Cb (FIG. 1a). Ir is a water-soluble derivative of camptothecin and a potent DNA topoisomerase I inhibitor in cancer cells, which induces the death of tumor cells through DNA damage and transcription inhibition; while Cb is one of water-insoluble DNA-alkylating anticancer drugs. Both Ir and Cb have been approved by Food and Drug Administration (FDA). (Husain, et al. 1994 Cancer Rev. 54, 539-546; Pommier, et al. 2006 Nat. Rev. Cancer 6, 789-802.) Ascribing to its amphiphilic structure, the Ir-Cb ADDC can self-assemble into nanoparticles in water to deliver themselves into tumor tissues by passive accumulation via EPR effect (FIG. 1b,c). (Maeda, et al. 1992 Bioconjug. Chem. 3, 351-362; Lyer, et al. 2006 Drug Discov. Today 11, 812-818.) After the cellular internalization of Ir-Cb ADDC nanoparticles, both free Ir and Cb can be released to kill the cancer cells due to the hydrolysis of the ester bond in tumor cells (FIG. 1d,e).

Synthesis of Ir-Cb ADDC

The amphiphilic Ir-Cb conjugate was synthesized by esterification in DCC/DMAP-catalyzed system (DCC: dicyclohexylcarbodiimide; DMAP: 4-dimethylamio-pyridine) as shown in Scheme 1.

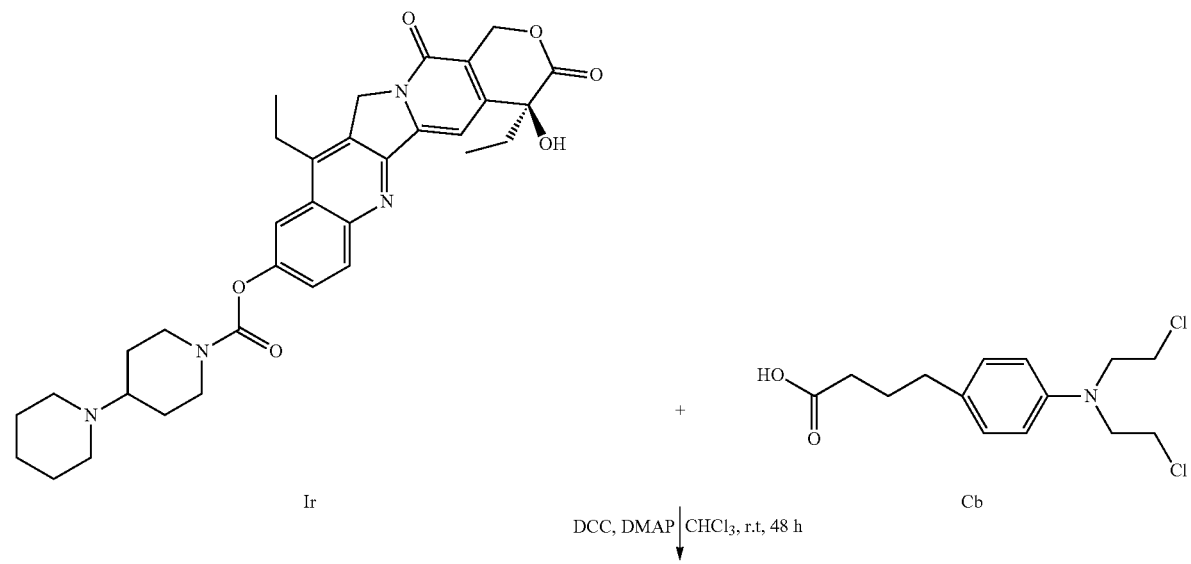

Scheme 1. Synthesis route of Ir-Cb ADDC.

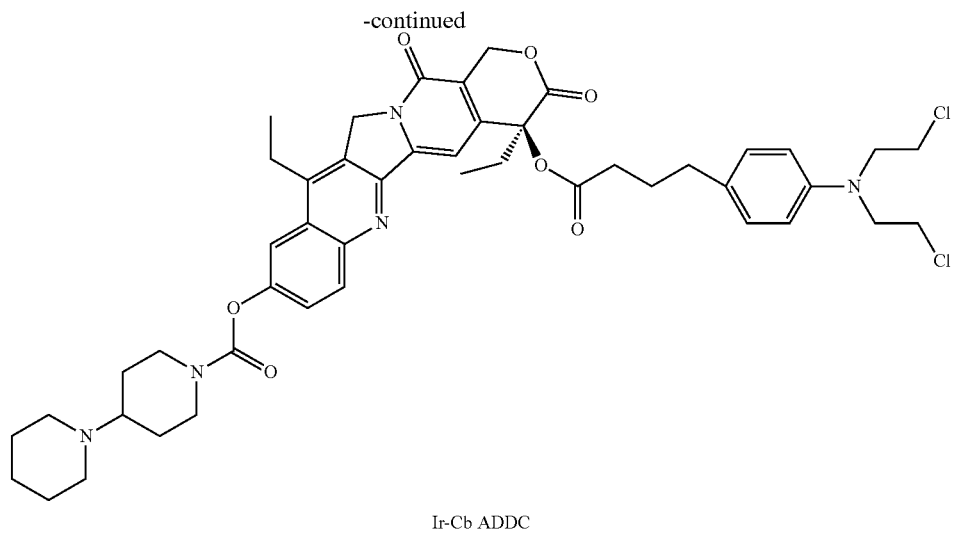

Ir-Cb ADDC

The chemical structure of Ir-Cb conjugate was confirmed by $^1$H and $^{13}$C nuclear magnetic resonance spectroscopy ($^1$H and $^{13}$C NMR), mass spectrometry (MS), Fourier transform infrared spectrometer (FTIR) spectra, and ultraviolet-visible spectrophotometer (UV-Vis) techniques (FIGS. 2-6).

Self-Assembly of Ir-Cb ADDC.

Figure 7:
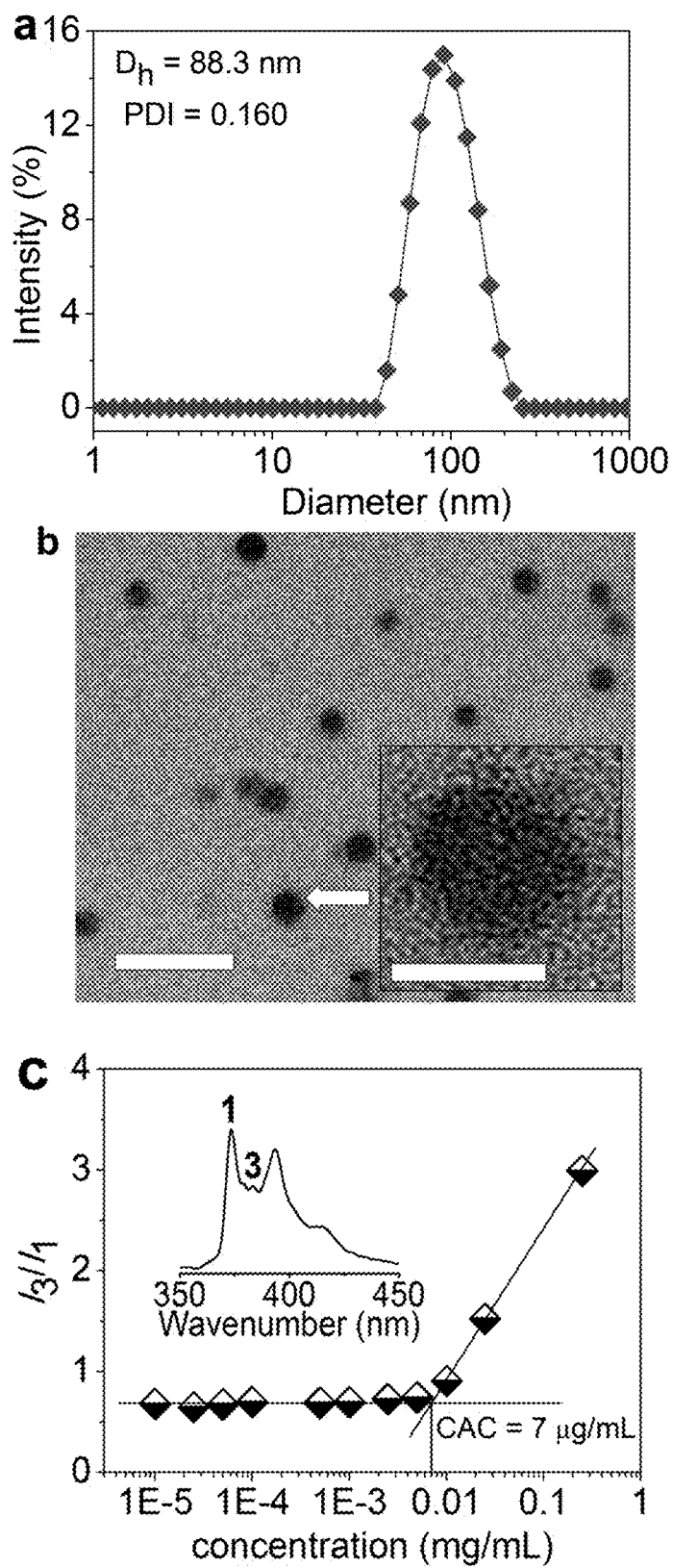
FIG. 7. a, DLS curve of Ir-Cb ADDC nanoparticles shows the diameter distribution of the nanoparticles, the polydispersity index (PDI=0.160) and the average size ($D_h$=88.3 nm). Inset: a digital photograph of Ir-Cb ADDC nanoparticle solution, exhibiting a stable, transparent bluish solution. b, TEM image of Ir-Cb ADDC nanoparticles. Inset: the amplified image of a nanoparticle. Scale bars: 200 nm (e), 50 nm (inset). c, Relationship between the fluorescent intensity ratio ($I_3/I_1$) and Ir-Cb ADDC concentration in water. Inset: the fluorescence emission spectrum of pyrene in aqueous solution. The CAC value is about 7 μg mL$^{-1}$.

The inherent amphiphilicity of the Ir-Cb ADDC provides an opportunity for itself to self-assemble into nanoparticles in water. To determine the size and morphology of the self-assembled nanoparticles, a dimethylsulfoxide (DMSO) solution of the Ir-Cb ADDC was added dropwise into water, followed by dialysis against water to remove DMSO. A stable and bluish solution with the final Ir-Cb conjugate concentration of 0.5 mg mL$^{-1}$ was obtained. FIG. 7a gives the dynamic light scattering (DLS) curve of Ir-Cb ADDC aqueous solution with a concentration of 0.5 mg mL$^{-1}$, indicating the formation of aggregates with a narrow unimodal distribution and an average hydrodynamic diameter of approximate 88.3 nm. The morphology of the aggregates was observed by transmission electron microscopy (TEM). The TEM image in FIG. 7b shows the spherical nanoparticles with an average size of approximate 75.7 nm. This size is slightly smaller than that measured by DLS due to the shrinkage of nanoparticles in a drying state during TEM sample preparation. The inset of FIG. 7b presents a typical enlarged TEM image of one nanoparticle. It clearly indicates that this nanoparticle consists of a lot of small spherical domains. Thereby, it is deduced that the nanoparticles are a type of multi-micelles aggregates (MMA), which has been well reported previously. (Mai, et al. 2005 *Macromolecules* 38, 8679-8686; Radowski, et al. 2007 *Chem., Int. Ed.* 46, 1265-1269.)

To investigate the self-assembly behavior of Ir-Cb ADDC in water, the critical aggregation concentration (CAC) was measured by using pyrene as a fluorescent probe. $I_1$ and $I_3$ are the emission intensities of the first and third bands in the fluorescence spectrum of pyrene respectively, which are labeled as 1 and 3 in the inset of FIG. 7c. The emission intensity ratio of $I_3/I_1$ is very sensitive to the polarity of the medium surrounding pyrene molecules. (Kwon, et al. 1993 *Langmuir* 9, 945-949.) The higher polarity of the medium, the lower the intensity ratio is. The relationship of the $I_3/I_1$ ratio with the Ir-Cb ADDC concentration is present in FIG. 7c. At low Ir-Cb ADDC concentration, the $I_3/I_1$ value remains nearly unchanged, indicating the characteristics of pyrene in water environment. With increasing Ir-Cb ADDC concentration, the ratio of $I_3/I_1$ starts to increase dramatically and reaches the characteristic level of pyrene in hydrophobic environment at a certain Ir-Cb ADDC concentration. According to the inflexion of the curve, the CAC value of the Ir-Cb ADDC is about 7 μg mL$^{-1}$.

In Vitro Drug Release.

Figure 8:
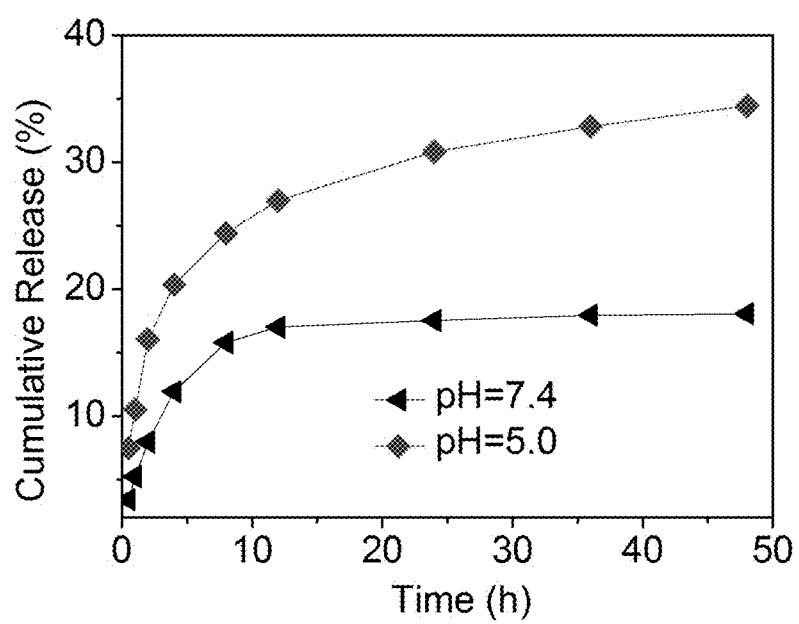
FIG. 8. In vitro Ir release kinetics from Ir-Cb ADDC nanoparticles under different pH values (7.4 and 5.0) at 37° C.

The in vitro release behavior of Ir-Cb ADDC nanoparticles was evaluated by dialysis in two different buffered solutions (pH 7.4 and 5.0) at 37° C. The cumulative release curves in FIG. 8 show that the concentration of released Ir is low at the pH value of 7.4, suggesting the good stability of Ir-Cb ADDC nanoparticles under physiological condition. However, at a weakly acidic environment (pH 5.0), the hydrolysis of Ir-Cb ADDC is accelerated and more free Ir and Cb drugs are released.

In Vitro Activity of Ir-Cb ADDC Nanoparticles.

The proliferation inhibition of Ir-Cb ADDC nanoparticles was evaluated against MCF-7 (a human breast adenocarcinoma cell line) and HeLa (a human cervical carcinoma cell line) cancer cells, comparing with free Cb, Ir and Ir/Cb mixture. The cells without any treatment were used as the control. As displayed in FIG. 9a, the cytotoxicity to MCF-7 cancer cells of free Ir and Ir/Cb mixture is nearly the same but much higher than that of free Cb, probably due to the difficult uptake of hydrophobic Cb by tumor cells. The therapeutic efficacy of Ir-Cb ADDC is strongly dependent on drug concentration. If the drug concentration is lower than the CAC value, the antitumor activity of Ir-Cb ADDC is worse than that of free Ir and Ir/Cb mixture. When the concentration of Ir-Cb ADDC is higher than the CAC value, it shows much better anticancer efficiency than free Ir and Ir/Cb mixture. The higher anticancer efficacy suggests that the self-assembled Ir-Cb ADDC nanoparticles enter into tumor cells, and the released free Ir and Cb might play a synergistic action. The similar phenomenon is also found in other cancer cell lines such as HeLa cells (FIG. 9b).

Figure 10:
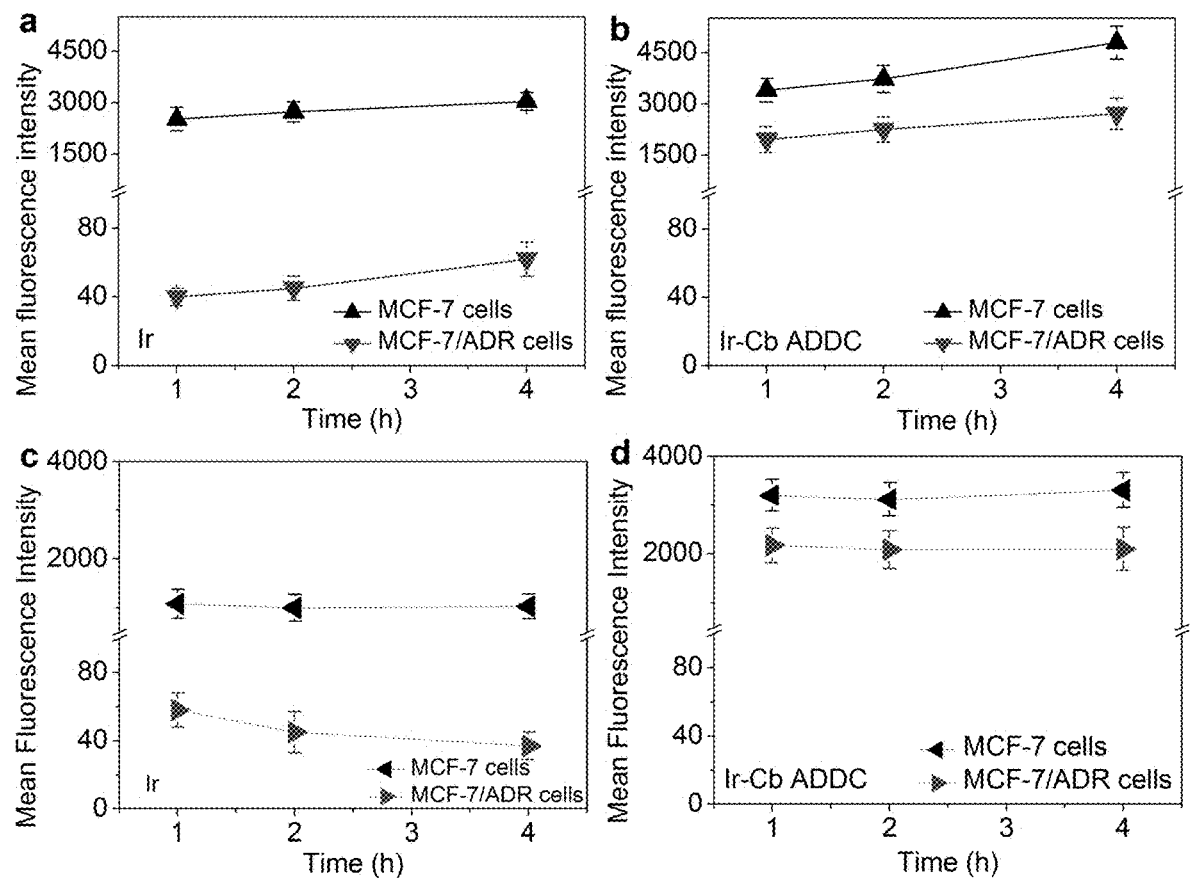
FIG. 10. a, The accumulation of free Ir in MCF-7 cells and MCF-7/ADR cells after incubation with Ir for different time. b, The accumulation of Ir-Cb ADDC in MCF-7 cells and MCF-7/ADR cells after incubation with Ir-Cb ADDC nanoparticles for different time. c, The efflux of free Ir from MCF-7 cells and MCF-7/ADR cells. d, The efflux of Ir-Cb ADDC nanoparticles from MCF-7 cells and MCF-7/ADR cells. Cells were first treated with free Ir and Ir-Cb ADDC nanoparticles for 4 h, and then incubated with fresh medium for various time.

MDR studies of Ir-Cb ADDC nanoparticles. MDR is one major cause of treatment failure clinically for cancer therapy, especially for small molecular anticancer drugs. One of the main mechanisms of MDR is drug efflux mediated by transporters such as P-glycoprotein (P-gp), which belongs to the ATP-binding cassette (ABC) family of membrane transporters. P-gp can use the energy from ATP-hydrolysis to pump free small molecular anticancer drugs out of tumor cells, resulting in a reduction of the drug accumulation in tumor cells. (Gottesman, et al. 2002 *Nat. Rev. Cancer* 2, 48-58; Shapira, et al. 2011 *Drug Resist. Updates* 14, 150-163.) Fortunately, the nanoparticles can bypass the P-gp efflux pump, accumulate themselves in cells and deliver drugs into cytoplasm efficiently. (Chacanpatil, et al. 2007 *Mol. Pharm.* 4, 730-738; Iversen, et al. 2011 *Nano Today* 6, 176-185.) Hence, the Ir-Cb ADDC nanoparticles are expected to overcome the MDR of tumor cells. The accumulation assay of free Ir and Ir-Cb ADDC nanoparticles was studied using drug-sensitive MCF-7 cells and drug-resistant MCF-7/ADR cells. Owing to the low expression of P-gp, the accumulation of free Ir in MCF-7 cells is rather high and increases with incubation time. Contrarily, the accumulation of free Ir in MCF-7/ADR cells is extremely low due to MDR, which decreases to 1/50~1/60 compared with that in MCF-7 cells (FIG. 10a). Interestingly, remarkable accumulation is observed in both MCF-7 cells and MCF-7/ADR cells when incubation with Ir-Cb ADDC nanoparticles for the same period. The amount of Ir-Cb conjugate in MCF-7/ADR cells is about ½ to that in MCF-7 cells (FIG. 10b), which may attribute to the high cellular internalization of Ir-Cb ADDC nanoparticles and efficient resistance to P-gp mediated drug efflux. If the cells were first treated with free Ir and Ir-Cb ADDC nanoparticles for 4 h and then incubated with fresh medium for various time, the similar results were obtained, as shown in FIGS. 10c,d.

Figure 9:
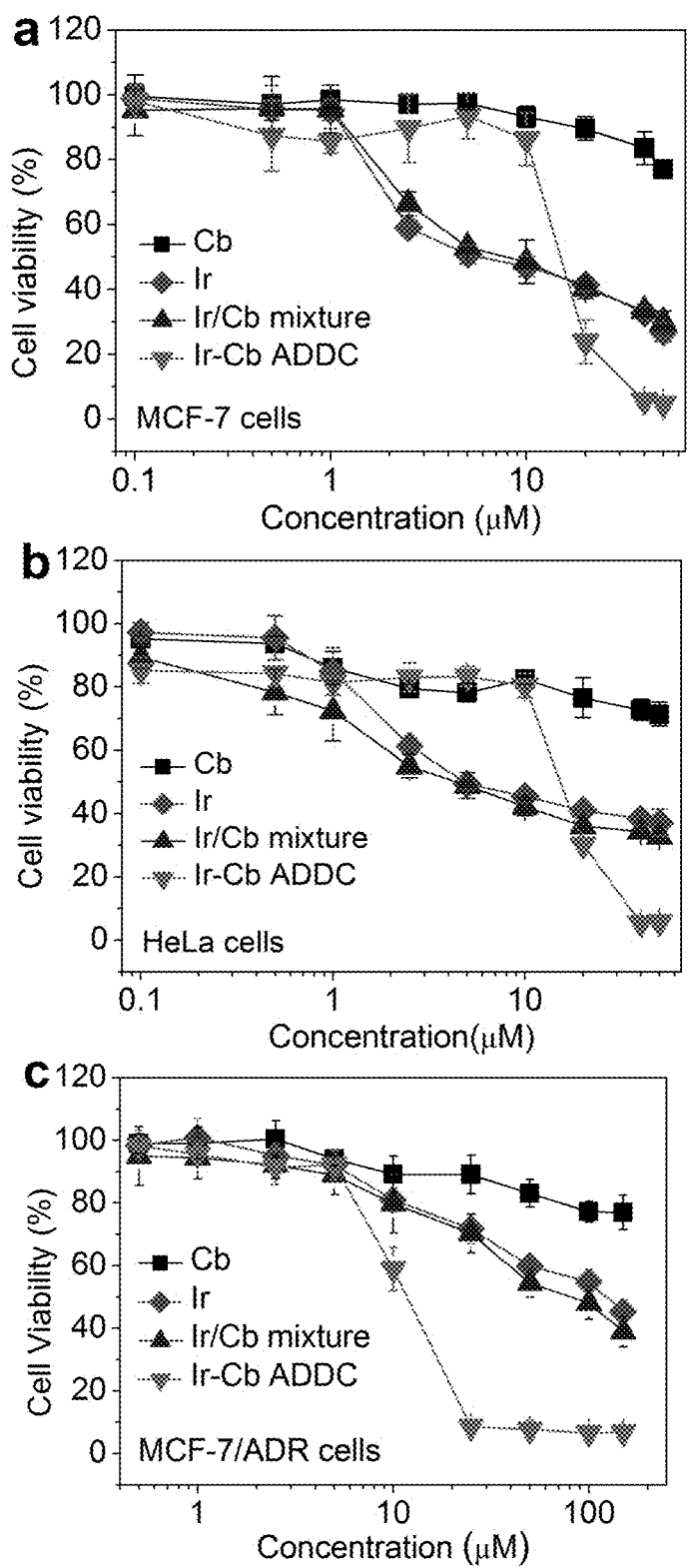
FIG. 9. In vitro cytotoxicity of Cb, Ir, Ir/Cb mixture, and Ir-Cb ADDC nanoparticles to MCF-7 cells (a), HeLa cells (b), and MCF-7/ADR cells (c) determined by MTT assay. The data are presented as average±standard error (n=6).

To further confirm the anticancer efficiency of Ir-Cb ADDC nanoparticles on MDR tumor cells, the cytotoxicity of various drug formulations was investigated by methyl tetrazolium (MTT) assay (FIG. 9c). In MCF-7/ADR cells, the half-maximal inhibitory concentration ($IC_{50}$) values of free Ir and Ir/Cb mixture are as high as 100 µM as the result of high overexpression of P-gp, which is ~20-fold resistance to Ir and Ir/Cb mixture by comparison to the MCF-7 ($IC_{50}$: ~5 µM, FIG. 9a). However, the $IC_{50}$ (~15 µM) of Ir-Cb ADDC nanoparticles in MCF-7/ADR cells is not significantly different from that (~13 µM) in MCF-7 cells (FIG. 9a,c). These observations demonstrate that the Ir-Cb ADDC nanoparticles can overcome the MDR of tumor cells.

Cell Apoptosis Assay.

Figure 11:
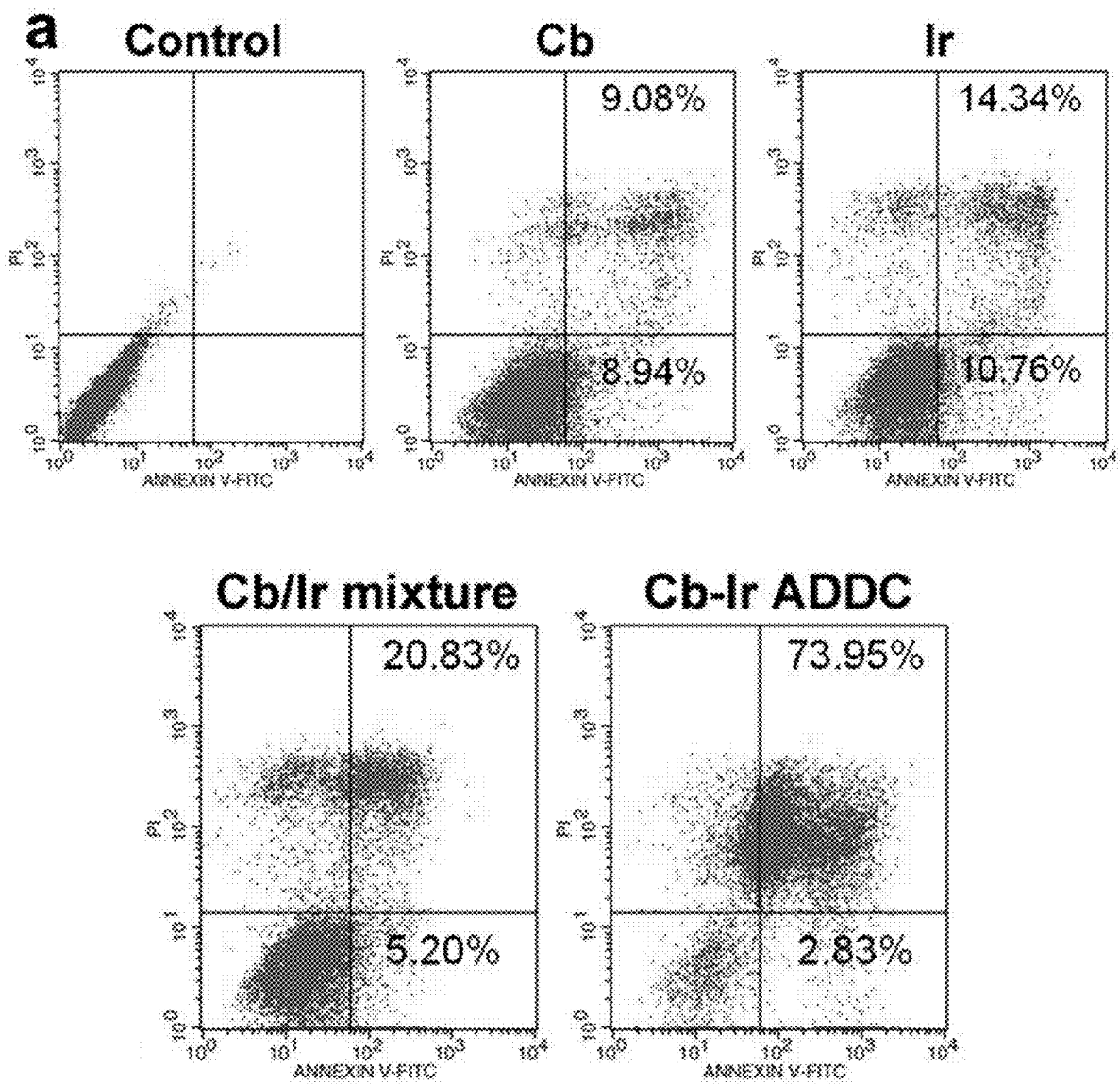
FIG. 11. a, Flow cytometry analysis for apoptosis of MCF-7 cells induced by Cb, Ir, Ir/Cb mixture and Ir-Cb ADDC nanoparticles at the same concentration of 30 μM for 24 h. Lower left: living cells; Lower right: early apoptotic cells; Upper right: late apoptotic cells; Upper left: necrotic cells. Inserted numbers in the profiles indicate the percentage of the cells present in this area. b, The expression levels of caspase-3 in MCF-7 cells induced by Cb, Ir, Ir/Cb mixture and Ir-Cb ADDC nanoparticles at the same concentration (30 μM) for 24 h, determined by western blot analysis. Cells untreated are used as a control, and β-actin is the loading control. Data represent three individual experiments. Each experiment group is repeated three times. c, The cell cycle distribution histograms of MCF-7 cells treated with Cb, Ir, Ir/Cb mixture and Ir-Cb ADDC nanoparticles at the same concentration of 30 μM for 24 h.
Figure 11:
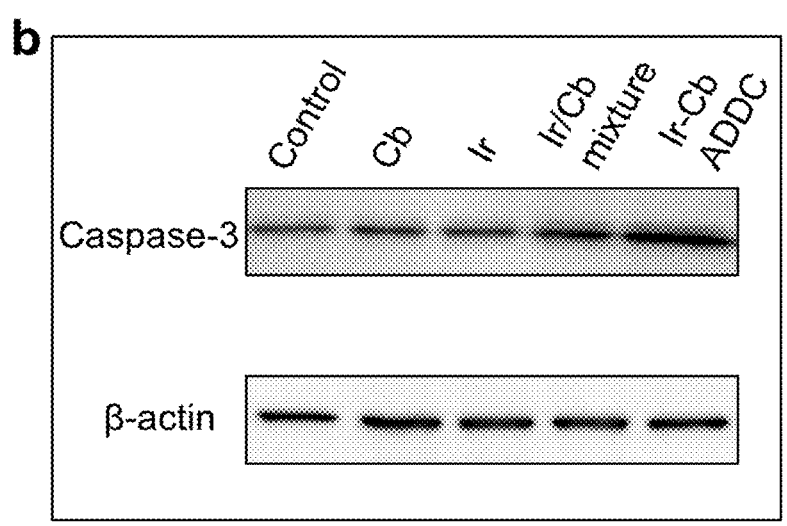
Figure 11:
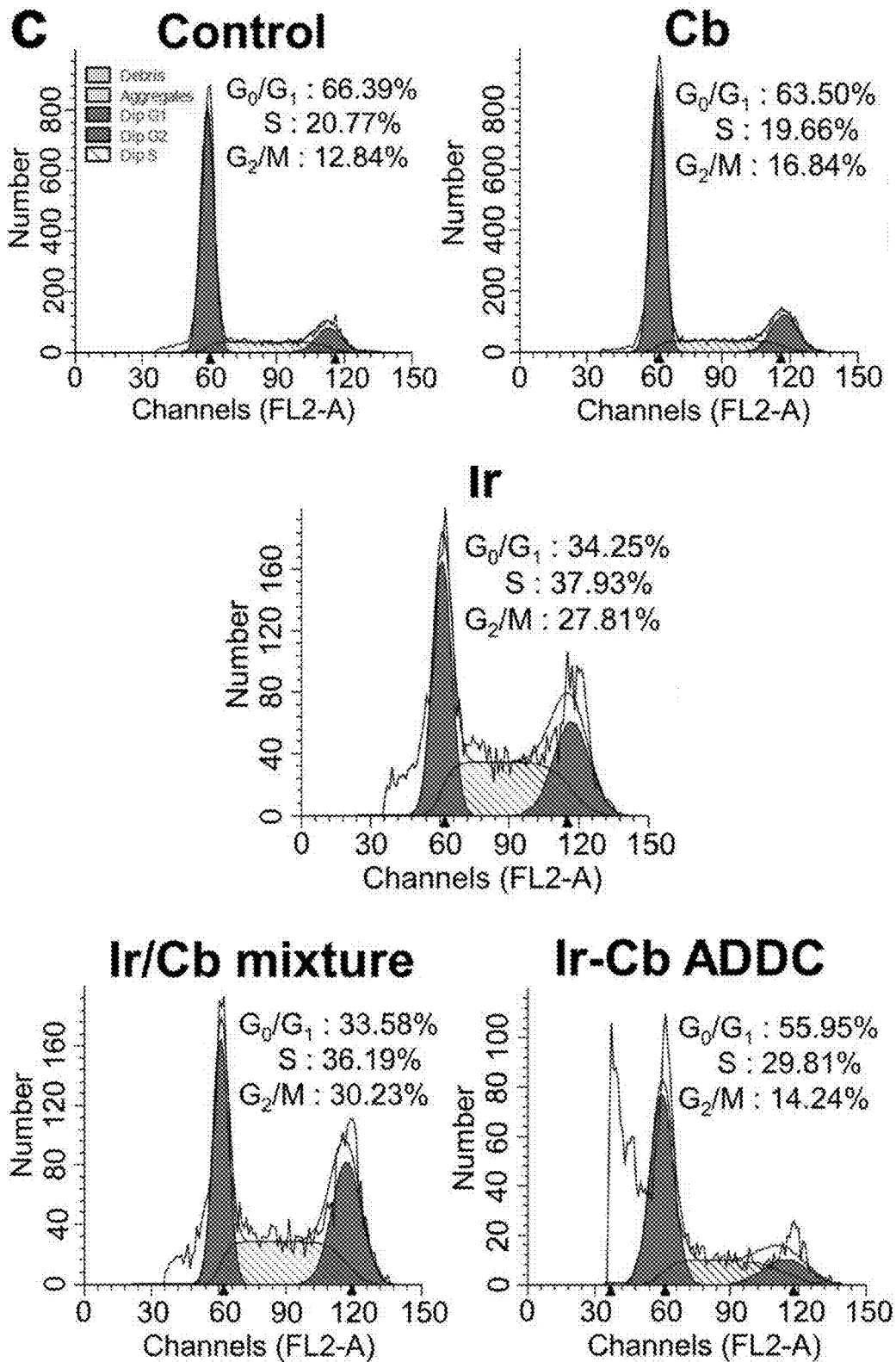

It is well known that most of small molecular anticancer drugs generally kill tumor cells by activating apoptosis. Here, FITC-Annexin V/propidium iodide (PI) method was used to determine whether the death of cancer cells incubating with Ir-Cb ADDC nanoparticles was induced by apoptosis. MCF-7 cells were first incubated with Cb, Ir, Ir/Cb mixture and Ir-Cb ADDC nanoparticles at the same concentration (30 µM) for 24 h and then subjected to FITC-Annexin V/PI staining. The untreated cells were used as control. The flow cytometry analysis shows that the ratio of apoptosis cells is 18.02%, 25.0% or 26.03% induced by Cb, Ir or Ir/Cb mixture, and increases to 76.87% if incubation with Ir-Cb ADDC nanoparticles (FIG. 11a). In comparison with other formulations, the Ir-Cb ADDC nanoparticles promote much higher apoptotic rate of MCF-7 cells with the same dose.

Western Blotting.

Caspases, as a family of intracellular cysteine-aspartyl proteases, play an essential role in apoptosis. Among them, caspase-3 has been considered as a key effector of cell apoptosis and identified as being activated in response to cytotoxic drugs. (Grafter, et al. 2000 *Curr. Opin. Struct. Biol.* 10, 649-254; Lazebnik, et al. 1998 *Science* 281, 1312-1316; Green 1998 *Cell* 94, 695-698.) To verify whether the caspase-3 was activated by Ir-Cb ADDC nanoparticles, western blot analysis was used to examine the expression of caspase-3 protein. Firstly, MCF-7 cells were incubated with Cb, Ir, Ir/Cb mixture and Ir-Cb ADDC nanoparticles at the same concentration for 24 h. The untreated MCF-7 cells were used as a negative control. The western blot data reveal that caspase-3 protein expression is up-regulated slightly by Cb, Ir and Ir/Cb mixture in comparison with untreated control, whereas the expression of caspase-3 protein is markedly enhanced by Ir-Cb ADDC nanoparticles (FIG. 11b). These results clearly indicate that although caspase-3 can be activated by various formulations, the Ir-Cb ADDC nanoparticles are the most effective one to promote the activation of caspase-3.

Cell Cycle Assay.

Also assessed was the effect of Ir-Cb ADDC nanoparticles on cell cycle by measuring DNA content with the help of flow cytometry. Firstly, cells were treated with Cb, Ir, Ir/Cb mixture and Ir-Cb ADDC nanoparticles for 24 h and then stained with PI. The results in FIG. 11c show that cells treated with Cb exhibit similar cell cycle with control cells. However, the cell cycle is significantly changed after incubation with Ir and Ir/Cb mixture: the percentage of $G_0/G_1$ phase decreases to 34.25% and 33.58%, the percentage of $G_2/M$ increases to 27.81% and 30.23%, while the percentage of S increases to 37.93% and 36.19%, respectively. When incubation with Ir-Cb ADDC nanoparticles, the cell cycle changes and shows an obvious sub-$G_0/G_1$ apoptotic phase. These results are consistent with apoptosis analysis.

Cellular Uptake of Ir-Cb Nanoparticles.

Figure 5:
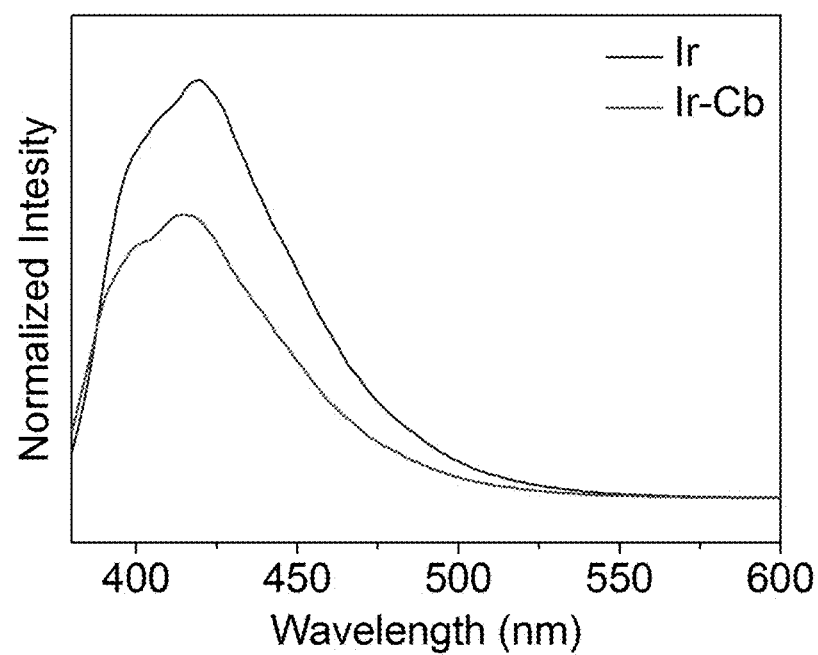
FIG. 5. Fluorescence emission spectra of Ir ($\lambda_{ex}$=363 nm, $\lambda_{em}$=420 nm) and Ir-Cb conjugate ($\lambda_{ex}$=360 nm, $\lambda_{em}$=415 nm) in acetonitrile.
Figure 6:
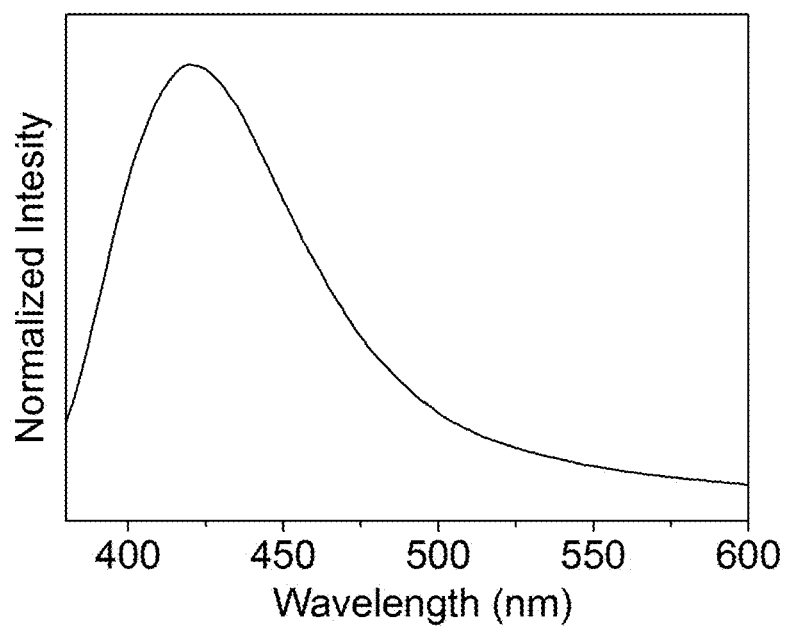
FIG. 6. Fluorescent emission spectrum of Ir-Cb ADDC nanoparticles in aqueous solution ($\lambda_{ex}$=360 nm, $\lambda_{em}$=420 nm).
Figure 12:
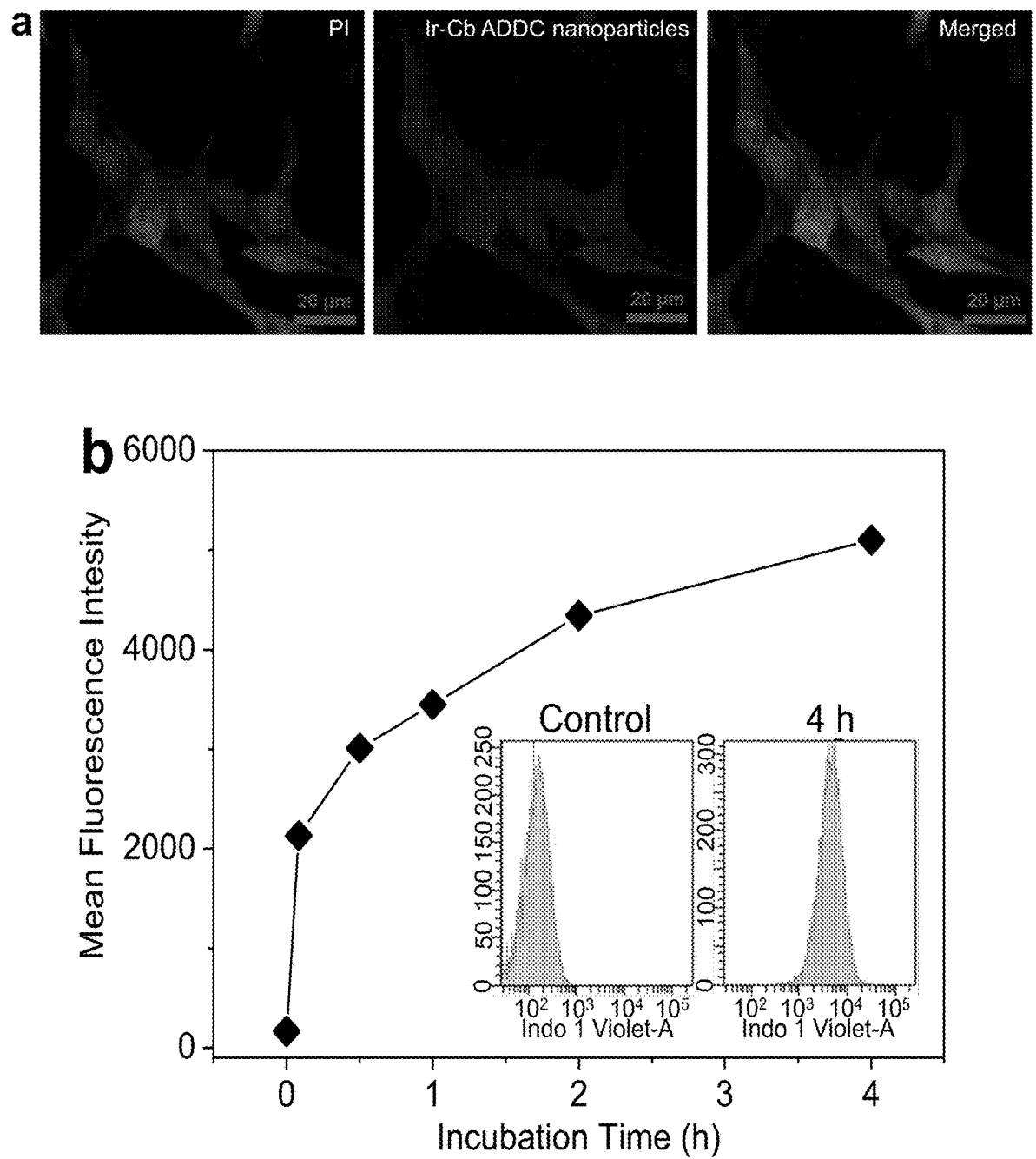
FIG. 12. a, CLSM photos of MCF-7 cells incubated with Ir-Cb ADDC nanoparticles for 4 h. Cell nuclei are stained with PI. b, Cellular uptake of Ir-Cb ADDC nanoparticles by MCF-7 cells versus the incubation time by flow cytometry analysis. Insert: representative flow cytometry histogram profiles of MCF-7 cells cultured with Ir-Cb nanoparticles for 4 h, the untreated cells are used as a control.

Ir emits blue fluorescence under UV-lamp irradiation. The fluorescence spectra of Ir and Ir-Cb ADDC in acetonitrile are shown in FIG. 5. The fluorescence spectroscopy studies in FIG. 6 show that the self-assembled Ir-Cb ADDC nanoparticles in water also emit strong blue fluorescence, suggesting that they can be used as probes for cell imaging. The cellular uptake of Ir-Cb ADDC nanoparticles was studied by confocal laser scanning microscopy (CLSM). MCF-7 cells were cultured with Ir-Cb ADDC nanoparticles for 4 h before observation. The nuclei were stained for 15 min with PI and the prepared cells were observed using a LEICA TCS SP8. As shown in FIG. 12a, the blue fluorescence of Ir-Cb ADDC nanoparticles is in both cytoplasm and nuclei according to the merged image. The results demonstrate that Ir-Cb ADDC nanoparticles could be internalized by the cells. The cellular uptake of Ir-Cb ADDC nanoparticles was further confirmed by flow cytometric analysis. FIG. 12b shows that the fluorescence intensity of cells increases with the incubation time, attributing to the cellular uptake of more and more Ir-Cb ADDC nanoparticles by MCF-7 cells.

Blood Retention Time and Biodistribution Studies.

Figure 13:
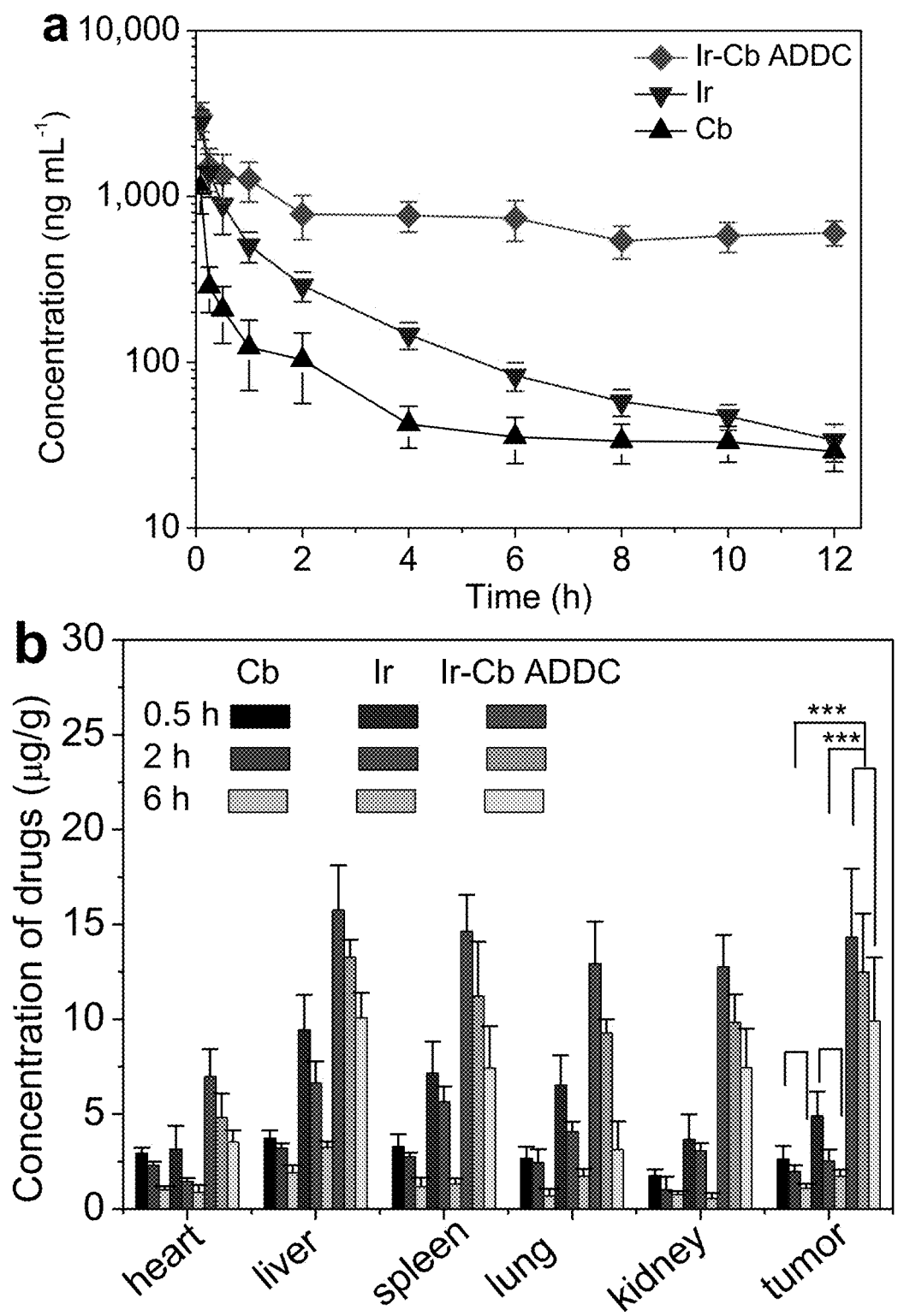
FIG. 13. a, Representative plasma concentration-time profiles of free Cb, Ir and Ir-Cb ADDC after i.v. injection into rats (a dose of 8 mg kg$^{-1}$). The data are presented as the average ±standard error (n=4). b, Tissue distribution of Cb, Ir and Ir-Cb ADDC after intravenous injection of free Cb (3.5 mg kg$^{-1}$), Ir (6.7 mg kg$^{-1}$) and Ir-Cb ADDC nanoparticles (10 mg kg$^{-1}$) in nude mice. Data are presented as average ±standard error (n=4) and the statistical significance level is ***P<0.001.

Comparing to free small molecular drugs, nanoparticles with a suitable size (<200 nm) usually show the longer retention time in the bloodstream. (Barreto, et al. 2011 *Adv. Mater.* 23, H18-H40.) To confirm this hypothesis, the pharmacokinetic study was undertaken by i. v. injection of the free Cb, Ir and Ir-Cb ADDC nanoparticles to Sprague-Dawley (SD) rats (~200 g). FIG. 13a gives the time profiles of the free Cb, Ir and Ir-Cb ADDC nanoparticles in plasma. It can be found that the Ir-Cb ADDC nanoparticles are retained at a higher concentration in the bloodstream up to 12 h, whereas the concentration of free Cb and Ir is only one twenty-fifth of the Ir-Cb ADDC after 12 h in the bloodstream. The longer circulation time of Ir-Cb ADDC nanoparticles enhances the accumulation of the drugs in the tumor tissues via the EPR effect.

Furthermore, to examine the amount of Ir-Cb ADDC in the tumors and other organs, the MCF-7 tumor-bearing mice were sacrificed after intravenous injection with different time intervals. The tumor-bearing mice treated with free Cb and Ir were used as controls. The biodistribution profiles show that a large amount of Ir-Cb ADDC accumulate in liver, spleen, kidney, lung and tumor at first 2 h. After injection for 6 h, the content of Ir-Cb ADDC obviously decreases in kidney, spleen and lung, whereas the downward trend in tumor and liver is slower (FIG. 13b). Compared to the Ir-Cb ADDC, the concentration of free Cb and Ir is remarkable lower in tumor and other organs. Ir mainly accumulates in liver, followed by spleen, lung, kidney and heart up to 2 h. After 6 h, the Ir concentration in spleen and lung decreases quickly. In contrast, Cb largely accumulates in liver, followed by spleen, lung, heart and kidney. These data indicate that Ir-Cb ADDC nanoparticles can be accumulated in tumors by passive targeting through EPR effect.

In Vivo Antitumor Activity Studies of Ir-Cb ADDC Nanoparticles.

Figure 14:
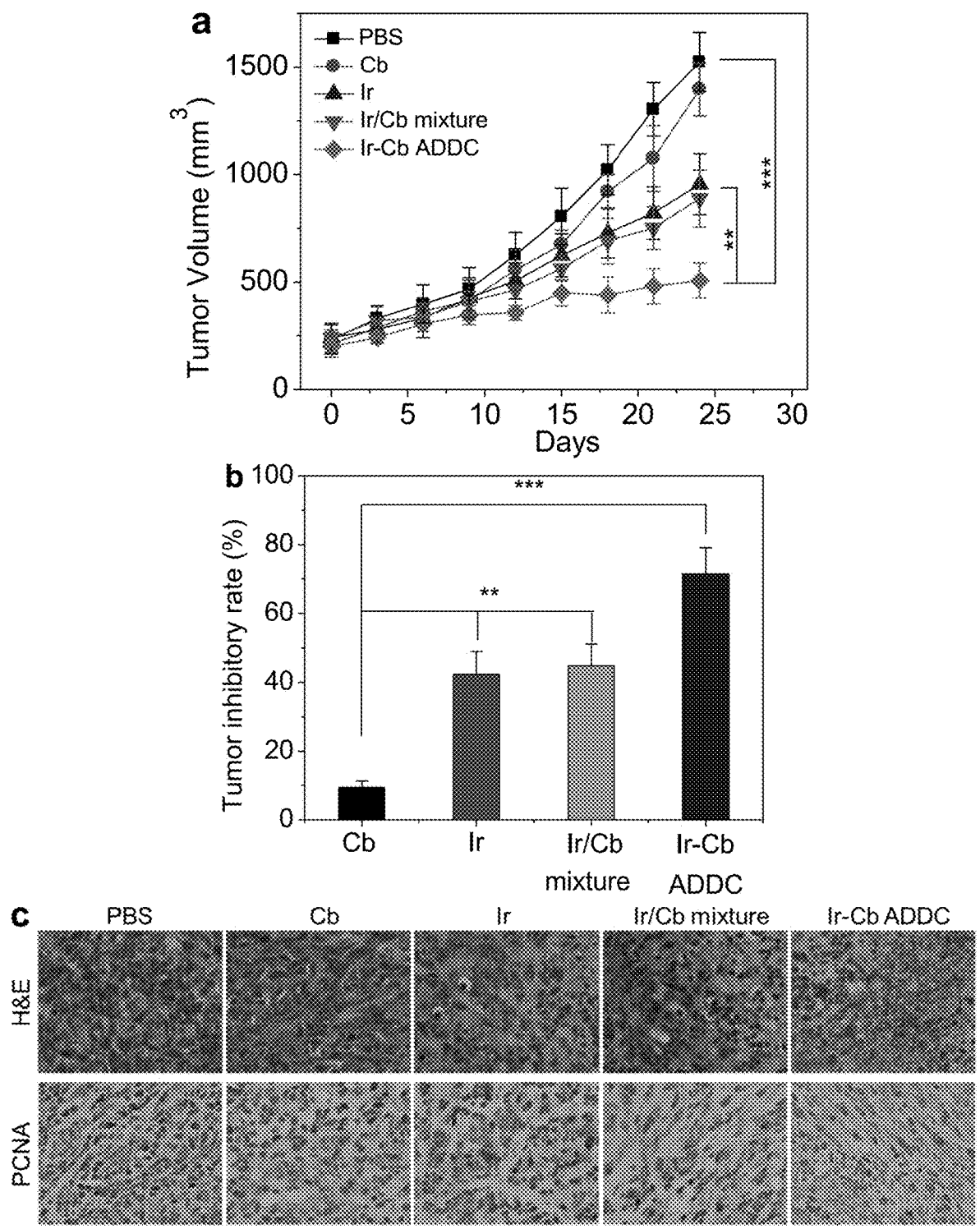
FIG. 14. a, Changes of tumor volume after intravenous injection of PBS, Cb, Ir, Ir/Cb mixture and Ir-Cb ADDC nanoparticles in MCF-7 tumor-bearing nude mice. b, The tumor inhibitory rate (TIR) after treated with Cb, Ir, Ir/Cb mixture and Ir-Cb ADDC nanoparticles in MCF-7 tumor-bearing nude mice. The TIR is calculated using the following equation: TIR=100%×(mean tumor weight of control group−mean tumor weight of experimental group)/mean tumor weight of control group. Data are represented as average ±standard error (n=6). Statistical significance: P<0.005; *P<0.001. c, Immunohistochemical analysis of tumor tissues treated with various treatments. Tumors are sectioned and stained with H&E. Tumor sections are evaluated for PCNA expression using an anti-mouse PCNA antibody (magnification×400).

To evaluate whether the efficient targeting and improved biodistribution results in the enhancement of therapeutic efficacy, MCF-7 tumor-bearing mice were intravenously injected with Cb, Ir, Ir/Cb mixture, Ir-Cb ADDC nanoparticles, and phosphate buffer solution (PBS) as control via the tail vein. Tumor volume and body weight of tumor-bearing mice were monitored every 3 days within 24 days. At the end of experiments, the tumor volumes (FIG. 14a) in mice treated with Ir-Cb ADDC nanoparticles were much smaller than those treated with PBS, Cb, Ir and Ir/Cb mixture. Compared with the PBS group, the tumor volume after 24 days treatment is 91.60±2.09% for Cb, 62.65±5.26% for Ir, 58.31±7.34% for Ir/Cb mixture or 32.11±3.07% for Ir-Cb ADDC nanoparticles, which shows that Ir-Cb ADDC nanoparticles procure predominant tumor growth inhibitory efficacy than Cb, Ir and Ir/Cb mixture. Meanwhile, no obvious change in efficacy is observed between Ir and Ir/Cb mixture groups. For the Cb formulation, no significantly therapeutic efficacy is found. These observations are in accordance with the results of in vitro evaluations. The tumor inhibitory rate (TIR) was calculated from tumor weight. Compared with the PBS group, the TIR of Ir-Cb ADDC nanoparticles is 71.40±7.75%, which is significantly higher than that of Cb (9.3±2.10%), Ir (42.3±6.63%) and Ir/Cb mixture (44.8±6.31%) (FIG. 14b). These results further demonstrate that the therapeutic efficacy of Ir-Cb ADDC nanoparticles is the highest in all of therapeutic groups.

Immunohistochemical Analysis.

3 days after the last injection, mice were sacrificed and tumor tissues were excised. The tissues were fixed in 10% formalin and embedded in paraffin. The paraffin-embedded 5 μm tumor sections were analyzed by immunohistochemical analysis for PCNA expression. To analyze the PCNA, endogenous peroxidase activity was inhibited by 3% hydrogen peroxide aqueous solution for 10 min, and the sections were heated to boiling in 0.01 M sodium citrate buffer (pH 6.0) for 10 min in the microwave oven for antigen retrieval and repeated boiling process for once. Subsequently, the sections were allowed to cool in the same buffer, rinsed twice with PBS for 5 min and then incubated with PCNA antibody (Boster, China, 1:200) for 30 min at room temperature and then at 4° C. overnight. After washing, sections were incubated with biotinylated secondary antibodies for 20 min at 37° C. Finally, a streptavidin-biotin complex was applied and the immunoreactivity was visualized with diaminobenzidine as a chromogen. The sections were imaged by using Olympus Fluorescence Microscope (Olympus BX61).

The immunohistochemical analysis was adopted to assess the different antitumor efficacy after treatment with various formulations. Histological examination of hematoxylin and eosin (H&E) stained tissue sections indicates obvious differences in tissue morphology between PBS and treated groups (FIG. 14c). The tumor cells treated with PBS group are observed with large nucleus and spindle shape in the tumor tissues, determining a rapid tumor growth. A similar result is achieved from treatment of Cb. By contrast, the tumor cellularity, as evaluated by average tumor cell numbers of each microscopic field, decreases significantly and nuclear shrinkage and fragmentation are observed in the Ir, Ir/Cb and Ir-Cb ADDC treated groups, especially for the Ir-Cb ADDC treated tumors. (Rajan 2004 Cancer 100, 1365-1373.) Meanwhile, a large necrotic area is observed in the Ir-Cb ADDC group. The proliferating cell nuclear antigen (PCNA) was used to analyze cell proliferation in the tumor tissues after treatment of various formulations. The results clearly indicate that the percentage of PCNA-positive (brown) tumor cells gradually decreases in the mice treated with various drug formulations compared with PBS group (FIG. 14c). However, the percentage of PCNA-positive tumor cells treated with Ir-Cb ADDC nanoparticles is the lowest one among the therapeutic groups, resulting from the tumor cell proliferation inhibition in MCF-7 tumor-bearing mice. Hence, both H&E and PCNA staining results confirm the superior in vivo antitumor efficacy of Ir-Cb ADDC nanoparticles.

Comparing to the conventional drug delivery systems based on nanocarriers, the self-assembled ADDC is a drug self-delivered system that avoids the side-effects of carriers completely. It is worth of mentioning that for in vivo experiments, the longer blood circulation time and the passive targeting ability of ADDC nanoparticles would further improve the chemotherapeutic efficiency for anticancer treatment.

Thus, disclosed herein is a novel drug delivery strategy for cancer therapy through direct conjugation of a hydrophilic anticancer drug and a hydrophobic one. The amphiphilic drug-drug conjugate can self-assemble into nanoparticles in water, resulting in longer retention time than the corresponding free drugs in the bloodstream. The longer circulation time facilitates the accumulation of anticancer drugs in the tumor tissues via the EPR effect and the subsequent cellular internalization. After hydrolysis of the ADDC, the two released free anticancer drugs exert synergetic cytotoxicity to the tumor cells, showing higher anticancer activity than the individual free drugs. The ADDC nanoparticles in this study can be applied in clinic for the treatment of varieties of tumors.

In one aspect, the invention generally relates to an amphiphilic compound comprising a hydrophilic moiety and a hydrophobic moiety conjugated via a linkage capable of cleavage under an acidic condition, wherein each of the hydrophilic moiety and the hydrophobic moiety is independently an antitumor agent.

In certain embodiments, the linker comprises an ester bond.

In certain embodiments, the hydrophilic moiety is a DNA topoisomerase I inhibitor. In certain embodiments, the hydrophobic moiety is a DNA-alkylating agent.

In certain embodiments, the DNA topoisomerase I inhibitor is camptothecin or a derivative thereof. In certain embodiments, the DNA-alkylating agent is chlorambucil or a derivative thereof.

Examples of hydrophilic antitumor drugs having one or more hydroxyl groups include: Irinotecan, Topotecan, Lurtotecan, protonated Belotecan, Mitoxantrone, Ametantrone, protonated Doxorubicin, protonated Pirarubicin, protonated Aclacinomycin, Troxacitabine, Azacitidine, Cytarabine, Floxuridine, Fiudarabine 5'-Monophosphate, Pentostatin, Streptozocin, Gemcitabine, Zalcitabine, Emtricitabine, Decitabine, Fludarabine, Cladribine, Clofarabine, Isatiribine, Hydroxycarbamide, Streptozocin, Bleocin, Bleomycin, Apaziquone, Etoposide, Tiniposide, PF-0491502 (2-amino-8-((1r,4r)-4-(2-hydroxyethoxy)cyclohexyl)-6-(6-methoxypyridin-3-yl)-4-methylpyrido[2,3-d]pyrimidin-7(8H)-one), PF-04217903 (2-(4-(1-(quinolin-6-ylmethyl)-1H-[1,2,3]triazolo[4,5-b]pyrazin-6-yl)-1H-pyrazol-1-yl)ethanol), and all hydrophilic anticancer drugs with one or more hydroxyl group.

Examples of hydrophobic antitumor drugs having a carboxyl group include: Chlorambucil, Methotrexate, Edatrexate, Pralatrexate, Alitretinoin, Tretinoin, Bexarotene, Ibritumomab tiuxetan, Leucovorin, Porfimer, Streptonigrin, Gambogic acid, Pemetrexed, Raltitrexed, Cantharidin, Norcantharidin, Pseudolaric acid B, Melphalan, Atrasentan, 5,6-Dimethylxantheonone-4-acetic acid, Triterpenes with a carboxyl group, Diterpenes with a carboxyl group, Daphniphyllum B1 with a carboxyl group, Baicalin, Sulindacsulfone, E7974 ((S,E)-4-(S)-2-(R)-1-Sopropylpiperidine-2-carboxamido-N,3,3-trimethylbutanamido)-2,5-dimethylhex-2-enoic acid), Ganoderic acids T and Me, AKR501 (1-[3-Chloro-5-[[[4-(4-chloro-2-thienyl)-5-(4-cyclohexyl-1-piperazinyl)-2-thiazolyl]amino]carbonyl]-2-pyridinyl]-4-piperidinecarboxylic acid), TSU-68 (2-[(1,2-Dihydro 2-oxo-3H-indol-3-ylidene)methyl]-4-methyl-1H-pyrrole-3-propanoic acid), 4-[(4-Methylpiperazin-1-yl)methyl]benzoic acid, Bendamustine, Ubenimex, CPI-613 (6,8-Bis(benzylthio)octanoic acid), CGS-21680 (4-[2-[[6-Amino-9-(N-ethyl-β-Dribofuranuronamidosyl)-9H-purin-2-yl]amino]ethyl]-benzenepropanoic), Ursodiol (3α,7β-dihydroxy-5β-cholan-24-oic acid), Taltobulin (N,beta,beta-Trimethyl-L-phenylalanyl-N-[(1S,2E)-3-carboxy-1-(1-methylethyl)-2-butenyl]-N,3-dimethyl-L-valinamide), Talotrexin (2-[[(4S)-4-carboxy-4-[[4-[(2,4-diaminopteridin-6-yl)methylamino]benzoyl]amino]-butyl]carbamoyl]benzoicacid), MK-0752 (3-((1r,4s)-4-((4-chlorophenyl)sulfonyl)-4-(2,5-difluorophenyl)cyclohexyl)propanoic acid), Pelitrexol (N-[5-[2-[2-Amino-4-oxo-3,4,5,6,7,8-hexahydropyrido[2,3-d]pyrimidin-6(S)-yl]ethyl]-4-methylthien-2-ylcarbonyl]-L-glutamic acid), ANX-510 ((2S)-2-(4-(3-amino-1-oxo-5,6,6a,7-tetrahydroimidazo[1,5-f]pteridin-8(1H,4H,9H)-yl)benzamido)pentanedioic acid), OSI-027 (trans-4-[4-Amino-5-(7-methoxy-1Hindol-2-yl)imidazo[5,1-f][1,2,4]triazin-7-yl]cyclohexanecarboxylic acid), NM-3 (Isocoumarin, 2-(8-hydroxy-6-methoxy-1-oxo-1H-isochromen-3-yl)propanoic acid), and all hydrophobic anticancer drugs with one or more carboxyl group.

Compounds of the invention may be prepared by condensation or coupling reaction via any suitable reagents, for example, N,N'-Dicyclohexylcarbodiimide, N-Ethyl-N'-(3-dimethylaminopropyl)carbodimide hydrochloride. Catalysts may be used where appropriate, for example, 4-Dimethylaminopyridine.

Exemplary compounds include:

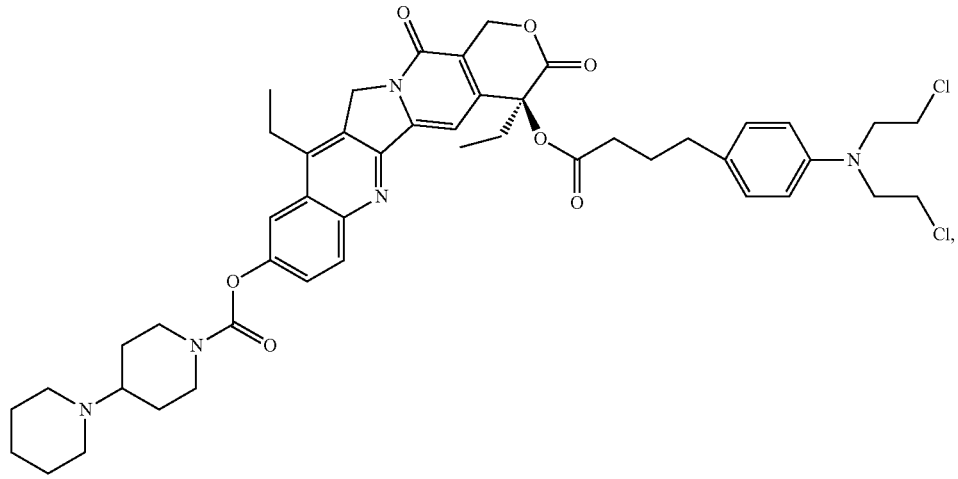 [SMILES: CCc1c2c(nc3ccc(OC(=O)N4CCC(N5CCCCC5)CC4)cc13)-c1cc3c(c(=O)n1C2)COC(=O)[C@@]3(CC)OC(=O)CCCc1ccc(N(CCCl)CCCl)cc1]

and derivative or analog amphiphilic compounds thereof made of two anticancer drugs;

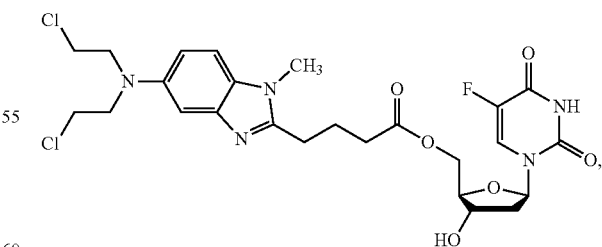

and derivative or analog amphiphilic compounds thereof made of two anticancer drugs;

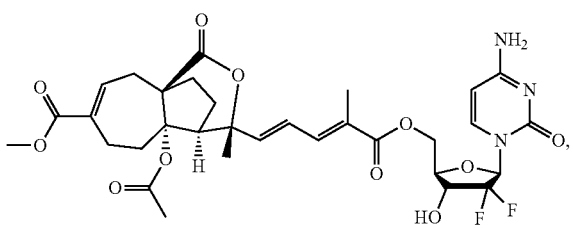

and derivative or analog amphiphilic compounds thereof made of two anticancer drugs;

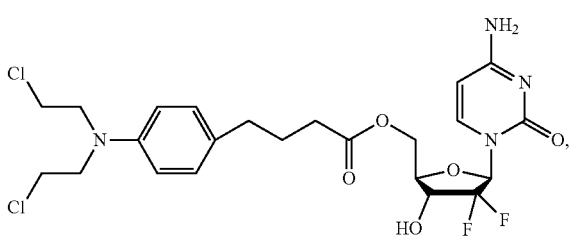

and derivative or analog amphiphilic compounds thereof made of two anticancer drugs;

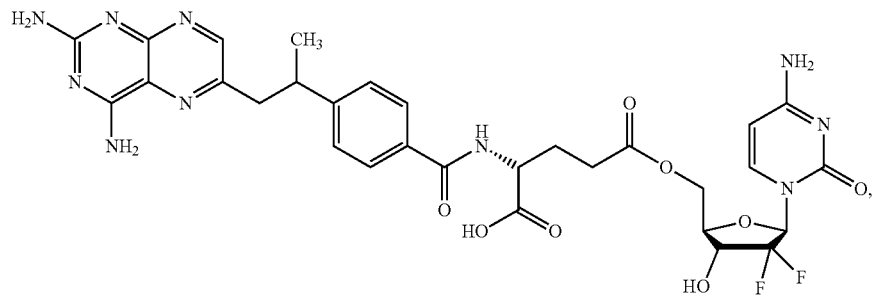

and derivative or analog amphiphilic compounds thereof made of two anticancer drugs.

In another aspect, the invention generally relates to a pharmaceutical composition comprising an amphiphilic compound disclosed herein, or a pharmaceutically acceptable ester thereof, in an amount effective in the treatment of cancer in a mammal, including a human. The pharmaceutical composition may comprise a pharmaceutically acceptable carrier.

In yet another aspect, the invention generally relates to a method of treating cancer, comprising administering to a subject in need thereof a therapeutically effective amount of a pharmaceutical composition comprising an amphiphilic compound disclosed herein, or a pharmaceutically acceptable ester thereof, effective in the treatment of cancer in a mammal, including a human. The pharmaceutical composition may comprise a pharmaceutically acceptable carrier. In yet another aspect, the invention generally relates to a nanoparticle comprising an amphiphilic compound disclosed herein.

In yet another aspect, the invention generally relates to a pharmaceutical composition comprising a nanoparticle disclosed herein in an amount effective in the treatment of cancer in a mammal, including a human. The pharmaceutical composition may comprise a pharmaceutically acceptable carrier.

In yet another aspect, the invention generally relates to a method of treating cancer, comprising administering to a subject in need thereof a therapeutically effective amount of a pharmaceutical composition comprising a nanoparticle disclosed herein, effective in the treatment of cancer in a mammal, including a human The pharmaceutical composition may comprise a pharmaceutically acceptable carrier.

In general, the "effective amount" of an active agent refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the patient.

Pharmaceutically acceptable salts, esters, prodrugs, tautomers, hydrates and solvates of the compounds presently disclosed are also within the scope of the present disclosure.

Presently disclosed compounds that are basic in nature are generally capable of forming a wide variety of different salts with various inorganic and/or organic acids. Although such salts are generally pharmaceutically acceptable for administration to animals and humans, it may be desirable in practice to initially isolate a compound from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds can be readily prepared using conventional techniques, e.g., by treating the base compound with a substantially equivalent amount of the chosen mineral or organic acid in an aqueous solvent medium or in a suitable organic solvent such as, for example, methanol or ethanol. Upon careful evaporation of the solvent, the desired solid salt is obtained.

Acids which can be used to prepare the pharmaceutically acceptable acid-addition salts of the base compounds are those which can form non-toxic acid-addition salts, i.e., salts containing pharmacologically acceptable anions, such as chloride, bromide, iodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

Presently disclosed compounds that are acidic in nature, e.g., contain a COOH or tetrazole moiety, are generally capable of forming a wide variety of different salts with various inorganic and/or organic bases. Although such salts are generally pharmaceutically acceptable for administration to animals and humans, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations, and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields of the desired solid salt.

Bases which can be used to prepare the pharmaceutically acceptable base-addition salts of the base compounds are those which can form non-toxic base-addition salts, i.e., salts containing pharmacologically acceptable cations, such as, alkali metal cations (e.g., potassium and sodium), alkaline earth metal cations (e.g., calcium and magnesium), ammonium or other water-soluble amine addition salts such as N-methylglucamine-(meglumine), lower alkanolammonium and other such bases of organic amines.

Isotopically-labeled compounds are also within the scope of the present disclosure. As used herein, an "isotopically-labeled compound" refers to a presently disclosed compound including pharmaceutical salts and prodrugs thereof, each as described herein, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

By isotopically-labeling the presently disclosed compounds, the compounds may be useful in drug and/or substrate tissue distribution assays. Tritiated ($^{3}H$) and carbon-14 ($^{14}C$) labeled compounds are particularly preferred for their ease of preparation and detectability. Further, substitution with heavier isotopes such as deuterium ($^{2}H$) can afford certain therapeutic advantages resulting from greater metabolic stability, for example increased in vivo half-life or reduced dosage requirements and, hence, may be preferred in some circumstances. Isotopically labeled compounds presently disclosed, including pharmaceutical salts, esters, and prodrugs thereof, can be prepared by any means known in the art.

Further, substitution of normally abundant hydrogen ($^{1}H$) with heavier isotopes such as deuterium can afford certain therapeutic advantages, e.g., resulting from improved absorption, distribution, metabolism and/or excretion (ADME) properties, creating drugs with improved efficacy, safety, and/or tolerability. Benefits may also be obtained from replacement of normally abundant $^{12}C$ with $^{13}C$. See, WO 2007/005643, WO 2007/005644, WO 2007/016361, and WO 2007/016431.

Stereoisomers (e.g., cis and trans isomers) and all optical isomers of a presently disclosed compound (e.g., R and S enantiomers), as well as racemic, diastereomeric and other mixtures of such isomers are within the scope of the present disclosure.

The present disclosure also provides pharmaceutical compositions comprising at least one presently disclosed compound and at least one pharmaceutically acceptable carrier. The pharmaceutically acceptable carrier can be any such carrier known in the art including those described in, for example, Remington's Pharmaceutical Sciences, Mack Publishing Co., (A. R. Gennaro edit. 1985). Pharmaceutical compositions of the compounds presently disclosed may be prepared by methods known in the art including, for example, mixing at least one presently disclosed compound with a pharmaceutically acceptable carrier.

Presently disclosed compounds can be formulated as a pharmaceutical composition for oral, buccal, parenteral (e.g., intravenous, intramuscular or subcutaneous), topical, rectal or intranasal administration or in a form suitable for administration by inhalation or insufflation.

The compounds presently disclosed may also be formulated for sustained delivery according to methods well known to those of ordinary skill in the art.

For oral administration, the pharmaceutical composition may take the form of, for example, a tablet or capsule prepared by conventional methods with a pharmaceutically acceptable excipient(s) such as a binding agent (e.g., pregelatinized maize starch, polyvinylpyrrolidone or hydroxypropyl methylcellulose); filler (e.g., lactose, microcrystalline cellulose or calcium phosphate); lubricant (e.g., magnesium stearate, talc or silica); disintegrant (e.g., potato starch or sodium starch glycolate); and/or wetting agent (e.g., sodium lauryl sulphate). The tablets may be coated by methods well known in the art. Liquid preparations for oral administration may take the form of a, for example, solution, syrup or suspension, or they may be presented as a dry product for constitution with water or other suitable vehicle before use. Such liquid preparations may be prepared by conventional methods with a pharmaceutically acceptable additive(s) such as a suspending agent (e.g., sorbitol syrup, methyl cellulose or hydrogenated edible fats); emulsifying agent (e.g., lecithin or acacia); non-aqueous vehicle (e.g., almond oil, oily esters or ethyl alcohol); and/or preservative (e.g., methyl or propyl p-hydroxybenzoates or sorbic acid).

For buccal administration, the composition may take the form of tablets or lozenges formulated in a conventional manner.

Presently disclosed compounds may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain a formulating agent such as a suspending, stabilizing and/or dispersing agent recognized by those of skill in the art. Alternatively, the active ingredient may be in powder form for reconstitution with a suitable vehicle, e.g., sterile pyrogen-free water, before use.

For topical administration, a presently disclosed compound may be formulated as an ointment or cream.

Presently disclosed compounds may also be formulated in rectal compositions such as suppositories or retention enemas, e.g., containing conventional suppository bases such as cocoa butter or other glycerides.

For intranasal administration or administration by inhalation, presently disclosed compounds may be conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the presently disclosed compound. Capsules and cartridges (made, for example, from gelatin) for use in an inhaler or insufflator may be formulated containing a powder mix of a presently disclosed compound and a suitable powder base such as lactose or starch.

A proposed dose of a presently disclosed compound for oral, parenteral or buccal administration to the average adult human for the treatment or prevention of an SK-related disease state is about 0.1 mg to about 2000 mg. In certain embodiments, the proposed dose is from about 0.1 mg to about 200 mg of the active ingredient per unit dose. Irrespective of the amount of the proposed dose, administration of the compound can occur, for example, 1 to 4 times per day.

Aerosol formulations for the treatment or prevention of the conditions referred to above in the average adult human are preferably arranged so that each metered dose or "puff" of aerosol contains about 20 µg to about 10,000 µg, preferably, about 20 µg to about 1000 µg of a presently disclosed compound. The overall daily dose with an aerosol will be within the range from about 100 µg to about 100 mg. In certain embodiments, the overall daily dose with an aerosol generally will be within the range from about 100 µg to about 10 mg. Administration may be several times daily, for example 2, 3, 4 or 8 times, giving for example, 1, 2 or 3 doses each time.

EXAMPLES

Materials.

N,N'-Dicyclohexylcarbodiimide (DCC, 99%, J&K), 4-(dimethylamino)pyridine (DMAP, 99%, J&K), tert-butyldimethylsilyl chloride (TBDMS-Cl, 99%, J&K), di-tert-butyl dicarbonate (Boc, 99%, J&K), triethylamine trihydrofluoride (TEA.3HF, 99%, J&K), trifluoroacetic acid (TFA, 99%, sigma), floxuridine (FdU, 99%, sigma), methotrexate (MTX, 98%, J&K), pyrene (98%, J&K), bendamustine (BdM, 98%, Fluka), dimethylthiazol-2-yl)-2,5-diphenytetrazolium bromide (MTT, 98%, sigma) chlorambucil (Cb, 98%, Fluka), and imidazole (99%, J&K) were used as received without further purification. Irinotecan (Ir) was purchased from Shanghai Knowshine Pharmachemical Inc. Gemcitabine hydrochloride (Gem.HCl) was purchased from Dalian Meilun Biology Technology Co. Ltd. Pseudolaric acid B (PAB) was provided from Shanghai Institute of Materia Medica, Chinese Academy of Sciences. Pyridine was dried by refluxing with potassium hydroxide (KOH) and distilled just before use. N,N-Dimethylformamide (DMF) was dried over calcium hydride and then purified by vacuum distillation. Triethylamine (TEA) was refluxed with phthalic anhydride, potassium hydroxide, and calcium hydride in turn and distilled just before use. Tetrahydrofuran (THF) and 1,4-dioxane were dried by refluxing with sodium wire under an argon atmosphere and distilled just before use. Dichloromethane (DCM) was dried over calcium hydride ($CaH_2$) and distilled just before use. All other reagents and solvents were purchased from the domestic suppliers and used as received.

Measurements.

$^1H$ and $^{13}C$ nuclear magnetic resonance ($^1H$ NMR and $^{13}C$ NMR) spectra were recorded using a Varian Mercury Plus 400 MHz spectrometer. Fourier transform infrared (FTIR) spectra were recorded on a Paragon 1,000 instrument by KBr sample holder method. Dynamic light scattering (DLS) measurements were performed under a Malvern Zetasizer 3,000 HS (Malvern Instruments, Ltd.) equipped with a 125 mW laser light and operated at λ=633 nm. All samples were measured at a scattering angle of 90°. Transmission electron microscopy (TEM) studies were performed with a JEOL 2010 instrument operated at 200 kV. The samples were prepared by directly dropping nanoparticle solution onto the carbon-coated copper grids and drying at room temperature overnight. Ultraviolet-visible (UV-Vis) absorption of the sample solutions was measured at room temperature by using a Thermo Electron-EV300 UV-Vis spectrophotometer. The slit-width was set as 1 nm with a scan speed of 480 nm $min^{-1}$. Fluorescent spectra were recorded on QC-4-CW spectrometer, made by Photon technology international, Int. USA/CAN. The excitation wavelength was set at 360 nm, which was chosen according to the maximum intensity obtained in the excitation spectra.

Example 1

Synthesis and Characterization of Ir-Cb ADDC

The amphiphilic Ir-Cb was synthesized by esterification in DCC/DMAP-catalyzed system and detailed procedure for Ir-Cb conjugate synthesis is described as follows: Cb (0.408 g, 1.34 mmol) and DCC (0.332 g, 1.61 mmol) were dissolved in dried $CHCl_3$ (10 mL), and the mixture was stirred at 0° C. After 30 min, the mixture was added to a solution of Ir (0.157 g, 0.268 mmol), DMAP (0.073 g, 0.6 mmol) and $CHCl_3$ (10 mL), and the resulting solution was stirred for 48 h at room temperature in the dark. Then the reaction mixture was filtered to remove white solids (dicyclohexylurea) and the filtrate was concentrated under vacuum. The crude product was purified by column chromatograph using dichloromethane ($CH_2Cl_2$) and dichloromethane/methanol ($CH_2Cl_2$:$CH_3OH$, 20:1 v/v) as the eluent. The product was collected and the solvent was removed by rotary evaporation to give a yellow solid (157 mg, 67%). $^1H$ NMR (400 MHz, $CDCl_3$) δ (ppm): 8.19-8.17 (d, J=8.8 Hz, 1H), 7.84 (s, 1H), 7.59 (dd, J=2.8 Hz, J=2.8 Hz, 1H), 7.17 (s, 1H), 7.07-7.05 (d, J=8.8 Hz, 2H), 6.59-6.57 (d, J=8.8 Hz, 2H), 5.70-5.66 (d, J=16.4 Hz, 1H), 5.43-5.39 (d, J=16.4 Hz, 1H), 5.24 (s, 2H), 4.50-4.39 (m, 2H), 3.69-3.65 (t, J=12.8 Hz, 4H), 3.61-3.58 (t, J=12.4 Hz, 4H), 3.18-3.06 (m, 4H), 2.95-2.88 (m, 1H), 2.59-2.55 (t, J=16.8 Hz, 2H), 2.78 (br, 4H), 2.31-2.26 (m, 2H), 2.52-2.43 (m, 2H), 2.19-2.10 (m, 2H), 1.96-1.89 (m, 2H), 1.83 (br, 8H), 1.41-1.37 (t, J=15.2 Hz, 3H), 0.99-0.95 (t, J=14.8 Hz, 3H). $^{13}C$ NMR (100 MHz, $CDCl_3$) δ (ppm): 172.73, 167.84, 157.59, 153.22, 151.80, 150.50, 147.39, 146.97, 146.17, 145.59, 144.54, 131.82, 130.58, 129.98, 127.77, 127.35, 126.04, 120.36, 114.86, 112.37, 96.06, 75.95, 67.36, 63.08, 53.81, 50.42, 49.49, 44.25, 43.81, 40.76, 33.87, 33.21, 32.09, 27.84, 27.05, 27.00, 25.09, 24.02, 23.40, 14.24, 7.81. ESI-MS m/z ($M+H^+$) calcd 872.3557, found 872.3547 ($M+H^+$).

Preparation of Ir-Cb ADDC Nanoparticles

In brief, 5 mg Ir-Cb ADDC was dissolved in 2 mL of DMSO and stirred at room temperature for 5 min. Then, the solution was slowly added to 4 mL of deionized water and stirred slightly for 30 min. Subsequently, the solution was dialyzed against deionized water for 24 h (molecular weight cutoff=1,000 g $mol^{-1}$), during which the water was renewed every 3 h. The volume of the solution was increased to 10 mL with the addition of deionized water to produce a solution with a concentration of 0.5 mg mL$^{-1}$ for further experiments.

Critical Aggregation Concentration (CAC) Measurement.

To determine the CAC value of the Ir-Cb ADDC, pyrene was used as the fluorescence probe. 3 μL of pyrene acetone solution (6×10$^{-4}$ mol L$^{-1}$) was added to 3 mL of Ir-Cb aqueous solution with different concentrations, while the concentration of pyrene in each flask was kept at 6×10$^{-7}$ mol L$^{-1}$. The fluorescence emission spectra of all samples were recorded on a LS-50B luminescence spectrometer (Perkin Elmer Co.) at 335 nm excitation wavelength and 8 nm slit width. The $I_3/I_1$ values of all solution were recorded.

Cell Culture.

HeLa cells, MCF-7 cells and MCF-7/ADR cells were cultured in Dulbecco's Modified Eagle's medium (DMEM). The culture mediums contain 10% FBS (fetal bovine serum) and antibiotics (50 units mL$^{-1}$ penicillin and 50 units mL$^{-1}$ streptomycin) at 37° C. under a humidified atmosphere containing 5% $CO_2$.

Cellular Uptake of Ir-Cb ADDC Nanoparticles by MCF-7 Cells.

The cellular uptake behaviors were studied in MCF-7 cells using flow cytometry and confocal laser scanning microcopy (CLSM). For flow cytometry, MCF-7 cells were seeded in 6-well plates at 5.0×10$^5$ cells per well in 2 mL of complete DMEM and cultured for 24 h. Then the solution of Ir-Cb ADDC nanoparticles was diluted with DMEM culture medium at a final concentration of 30 μM. The diluted solution was added to different wells and the cells were incubated at 37° C. for 5, 30, 60, 120 and 240 min. Thereafter, culture medium was removed and cells were washed with PBS for three times and treated with trypsin. Data for 1.0×10$^4$ gated events were collected and analysis was performed by means of a BD LSRFortessa flow cytometer. For the CLSM study, MCF-7 cells were seeded in 6-well plates at 2.0×10$^5$ cells per well in 1 mL of complete DMEM and incubated for 24 h, followed by removing culture medium and adding Ir-Cb ADDC nanoparticle solutions (0.5 mL DMEM medium) at the concentration of 30 μM. After incubation at 37° C. for 6 h, culture medium was removed, and cells were washed with PBS for two times. Subsequently, the cells were fixed with 4% formaldehyde for 30 min at room temperature, and the slides were rinsed with PBS three times. Finally, the cells were treated with 100 μL 10 mL$^{-1}$ propidium iodide (PI) solution and 0.5% triton solution at 37° C. for 15 min, and the slides were rinsed with PBS three times. The resulting slides were mounted and observed with a LEICA TCS SP8 fluorescence microscopy.

In Vitro Cytotoxicity Studies of Ir-Cb ADDC Nanoparticles.

The MCF-7 cells and HeLa cells were used to evaluate the anticancer activity of Ir-Cb ADDC nanoparticles. The free drug Ir and Cb and the mixture of Ir and Cb were used as control. The cells were seeded into 96-well plates at 1×10$^4$ cells per well in 200 μL of culture medium. After 12 h incubation, the medium was removed and replaced with 200 μL of a medium containing serial dilutions of Ir-Cb ADDC nanoparticles, free Ir and Cb, or the Ir/Cb mixture from 0.1 to 50 μM. The cells without the treatment were used as control. The cells were grown for another 72 h. Then, 20 μL of 5 mg mL$^{-1}$ MTT assay stock solution in PBS was added to each well. After the cells were incubated for 4 h, the medium containing unreacted MTT was carefully removed. Then, the obtained blue formazan crystals were dissolved in 200 μL well$^{-1}$ DMSO, and the absorbance was measured in a BioTek Synergy H4 hybrid reader at a wavelength of 490 nm. The blank was subtracted to the measured optical density (OD) values, and the cell viability was expressed as % of the values obtained for the untreated control cells.

The accumulation and efflux assay of Ir-Cb ADDC nanoparticles. MCF-7 cells and MCF-7/ADR cells were seeded in 24-well plates at a density of 5×10$^4$ per well in 0.5 mL of complete DMEM and incubated for 24 h. Then the cells were treated with free Ir and Ir-Cb ADDC nanoparticles for 1, 2 and 4 h at the same concentration (30 μM) at 37° C. At the end of experiment, the cells were washed for three times with ice-cold PBS and trypsinized, resuspended in 500 μL PBS. Data for 1.0×10$^4$ gated events were collected and analysis was performed by means of a BD LSRFortessa flow cytometer. The fluorescent intensity was calculated by CellQuest software, and blanked by untreated cells.

For drug efflux assay, MCF-7 cells and MCF-7/ADR cells were first cultured with free Ir and Ir-Cb ADDC nanoparticles for 4 h. Then, the medium was removed and the cells were washed with cold PBS for twice, followed by incubation with fresh medium for different time. The amounts of Ir and Ir-Cb in cells were determined by BD LSRFortessa flow cytometer.

Cell Apoptosis and Cell Cycle Assay.

MCF-7 cells were seeded in 6-well plates at 5.0×105 cells per well in 2 mL of complete DMEM and cultured for 24 h. The cells were treated with Cb, Ir, Ir/Cb mixture and Ir-Cb ADDC nanoparticles at the same concentration (30 μM) for 24 h. MCF-7 cells without the treatment were used as a control. For quantitative measurement of apoptosis, treated cells were harvested and washed twice with ice-cold PBS, stained with Alexa Fluor® 488 annexin V and PI according to the manufacturer's instructions. For cell cycle determination, treated cells were collected, washed for twice with ice-cold PBS, fixed with 70% ethanol at 4° C. overnight and treated with Rnase A for 45 min at 37° C., followed by PI staining for 30 min in the dark. Both cell apoptosis and cycle were analyzed by flow cytometry (BD FACSCalibur, USA), and 2×104 events per sample were counted.

Western Blot Analysis.

MCF-7 cells were seeded in 6-well plates at a density of 5.0×10$^5$ cells per well in 2 mL of complete DMEM and allowed to attach for 24 h. The cells were treated with Cb, Ir, Ir/Cb mixture and Ir-Cb ADDC nanoparticles at the same concentration (30 μM) for 24 h. MCF-7 cells untreated were used as a negative control. After treatment for 24 h, the MCF-7 cells were harvested. The cellular proteins were extracted in Laemmli buffer and the protein content in the extracts was quantified using a bicinchoninic acid (BCA) protein assay kit (Pierce, USA). Equal amounts of proteins (30 μg lane$^{-1}$) were separated on sodium dodecyl sulfate-polyacrylamide gels (SDS-PAGE) and electrotransferred to 0.22 μm polyvinylidene fluoride (PVDF) membranes. The membranes were then blocked with 5% non-fat dry milk in TBST (Tris buffered saline supplemented with 0.05% Tween-20) and probed with antibodies against β-actin (1:1, 000 dilution), caspase-3 (1:1,000 dilution) followed by HRP-conjugated (HRP: horseradish peroxidase) anti-rabbit immunoglobulin-G (IgG, 1:5,000 dilution). β-Actin was used as the loading control. Protein bands were detected using Chemiluminescent HRP Substrate (Themo Scientific, USA) according to the manufacture's protocol and analyzed using the ChemiDoc™ MP Imaging System (Bio-Rad, USA).

Animals and Tumor Models.

Study protocols involving animals were approved by the Animal Ethics Committee of Shanghai Jiao Tong University School of Medicine. SD rats (~200 g) and 72 Balb/c female nude mice (4 weeks of age) were supplied by Chinese Academy of Sciences (Shanghai). The female nude mice were injected subcutaneously in the right flank region with 200 μL of cell suspension containing $4 \times 10^6$ MCF-7 cells. The tumors were allowed to grow to ~200 $mm^3$ before experimentation.

Pharmacokinetic Studies.

SD rats (~200 g) were chosen to study the pharmacokinetics of Ir-Cb ADDC nanoparticles and free Cb and Ir. Rats were randomly divided into Ir-Cb ADDC nanoparticles and free Cb and Ir groups (n=4). The Ir-Cb ADDC, Cb and Ir solutions were intravenously injected via tail vein at a dose of 8 mg $kg^{-1}$. The blood samples (0.5 mL) were taken from the eye socket at the 5 min, 15 min, 30 min, 1 h, 2 h, 4 h, 6 h, 8 h, and 12 h time points after injection. The plasma was obtained by centrifugation at 3,000 rpm for 10 min and stored at −20° C. A 200 μL of plasma was treated two times with 250 μL of acetonitrile and methanol mixture (1:1 v/v). The solvent solutions separated by centrifugation were pooled. The samples of Ir-Cb and free Ir were directly examined by using fluorescence spectroscopy, and the samples of free Cb were measured by use of UPLC-3Q. The amounts of Ir-Cb ADDC, free Cb and Ir were obtained from standard curves previously obtained by analysis of blood samples containing known amounts of Ir-Cb, Cb and Ir.

In Vivo Biodistribution.

The biodistribution of Cb, Ir and Ir-Cb nanoparticles was analyzed in Balb/c female nude mice bearing MCF-7 tumors. The MCF-7 tumor-bearing mice were intravenously injected via tail vein with Cb, Ir and Ir-Cb nanoparticles at a dose of Cb (3.5 mg $kg^{-1}$), Ir (6.7 mg $kg^{-1}$) and Ir-Cb nanoparticles (10 mg $kg^{-1}$). Mice were sacrificed by cervical vertebra dislocation at 30 min, 1 h and 6 h after drug administration (n=3 at each time point), and the heart, liver, spleen, lung, kidney and tumor were collected. Tissue samples were rinsed in saline, blotted using paper towel, weighed and stored at −80° C. before being homogenized. Cb, Ir and Ir-Cb were extracted from the homogenate using 2 mL of dichloromethane and methanol (4:1, v/v). The organic phases were collected and dried, and the samples were dissolved in acetonitrile for analysis. The samples of Ir-Cb and free Ir were directly examined by using fluorescence spectroscopy, and the samples of free Cb were measured by use of UPLC-3Q. The amounts of Ir-Cb ADDC, Cb, and Ir were obtained from standard curves previously obtained by analysis of tissues samples containing known amounts of Ir-Cb, Cb and Ir.

In Vivo Anticancer Activity.

The MCF-7 tumor-bearing mice were randomly divided into five groups, and mice in different treatment groups were intravenously injected via the tail vein with PBS, Cb (3.5 mg $kg^{-1}$), Ir (6.7 mg $kg^{-1}$), Ir/Cb mixture (3.5 mg $kg^{-1}$ Cb and 6.7 mg $kg^{-1}$ Ir) and Ir-Cb ADDC nanoparticles (10 mg $kg^{-1}$) once every 3 days for 24 days. Each mouse of different group was earmarked and followed individually throughout the whole experiments. The length and width of the tumor and the body weight of mice were measured before every injection by the end of experiment. Tumor volume (V) was calculated using the formula: V $(mm^3) = \frac{1}{2} \times$ length (mm) $\times$ width $(mm)^2$. After 24 days postinjection, mice were sacrificed, and tumors were separated, weighted and photographed. In addition, the tumors were cut into small pieces, fixed in 10% formalin and embedded in paraffin. Then the tissues embedded in paraffin were sectioned for histopathological analysis with H&E staining.

Example 2

Synthesis of the FdU-BdM ADDC

In a typical procedure, FdU (280 mg, 1.14 mmol), DMAP (5 mg, 0.038 mmol), DCC (95 mg, 0.46 mmol) and TEA (53 μL, 0.38 mmol) were dissolved in anhydrous DMF (6 mL) and the mixture was stirred at room temperature under $N_2$. After 15 min, the BdM (53 μL, 0.38 mmol) in DMF (4 mL) was added dropwise and the reaction mixture was stirred for 48 h at room temperature. Then the reaction mixture was filtered to remove white solids (dicyclohexylurea) and the filtrate was concentrated under vacuum. The crude product was purified by column chromatograph using DCM/$CH_3OH$ (12:1, v/v) as the eluent. The product was collected and the solvent was removed by rotary evaporation to obtain FdU-BdM conjugate (155 mg, 69%). $^1H$ NMR (400 MHz, DMSO-$d_6$) δ (ppm) 11.85-11.84 (d, J=4.8 Hz, 1H), 7.91-7.90 (d, J=7.2 Hz, 1H), 7.32-7.30 (d, J=8.8 Hz, 1H), 6.89-6.88 (d, J=2.4 Hz, 1H), 6.78-6.76 (dd, J=8.8 Hz, 1H), 6.13-6.10 (t, J=13.2 Hz, 1H), 5.44-5.43 (d, J=4.4 Hz, 1H), 4.21-4.20 (d, J=4.8 Hz, 2H), 3.69 (m, 8H), 3.64 (s, 3H), 3.15-3.14 (t, J=5.2 Hz, 2H), 2.84-2.80 (t, J=14.8 Hz, 2H), 2.01 (m, 1H), 2.11 (m, 1H), 2.22-2.19 (t, J=13.2 Hz, 2H). $^{13}C$ NMR (100 MHz, DMSO-$d_6$) δ (ppm) 173.07, 162.98, 157.79, 154.80, 149.65, 143.20, 129.66, 125.57, 125.23, 111.01, 110.67, 102.42, 85.22, 84.47, 70.66, 64.51, 54.08, 42.08, 36.46, 33.33, 30.12, 26.10, 22.69. ESI-MS m/z $(M+H^+)$ calcd: 586.1637, found: 586.1649.

Synthesis of FdU-BdM ADDC

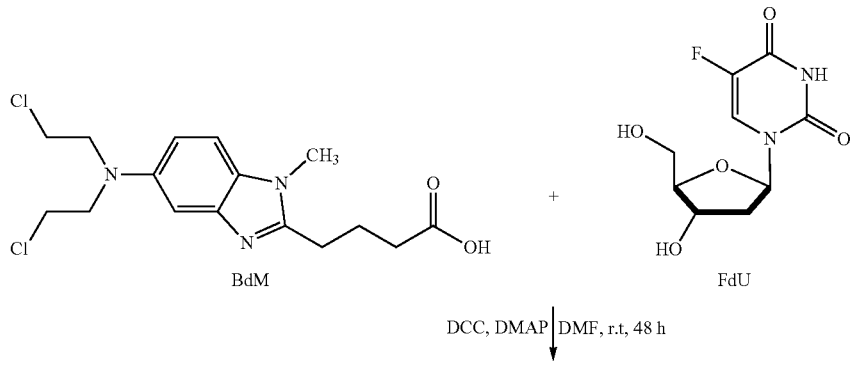

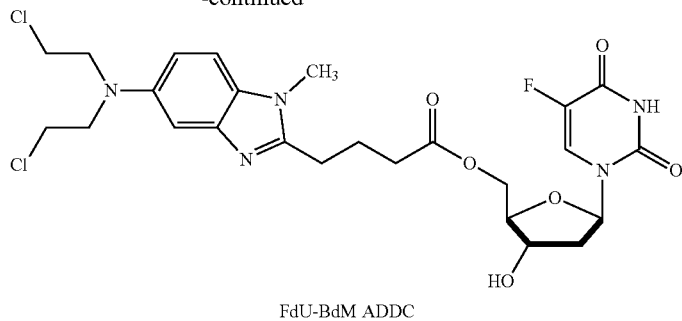

FdU-BdM ADDC

Preparation of FdU-BdM ADDC Nanoparticles

In brief, 3 mg FdU-BdM ADDC was dissolved in 3 mL of $CH_3OH$ and stirred at room temperature for 5 min. Then, 1 mL the $CH_3OH$ solution was added into 4 mL of deionized water by using a micro-syringe pump and stirred slightly for 30 min. Subsequently, the solution was dialyzed against deionized water for 24 h (molecular weight cutoff=3,000 g $mol^{-1}$). The final concentration of nanoparticles was 0.5 mg $mL^{-1}$.

Figure 15:
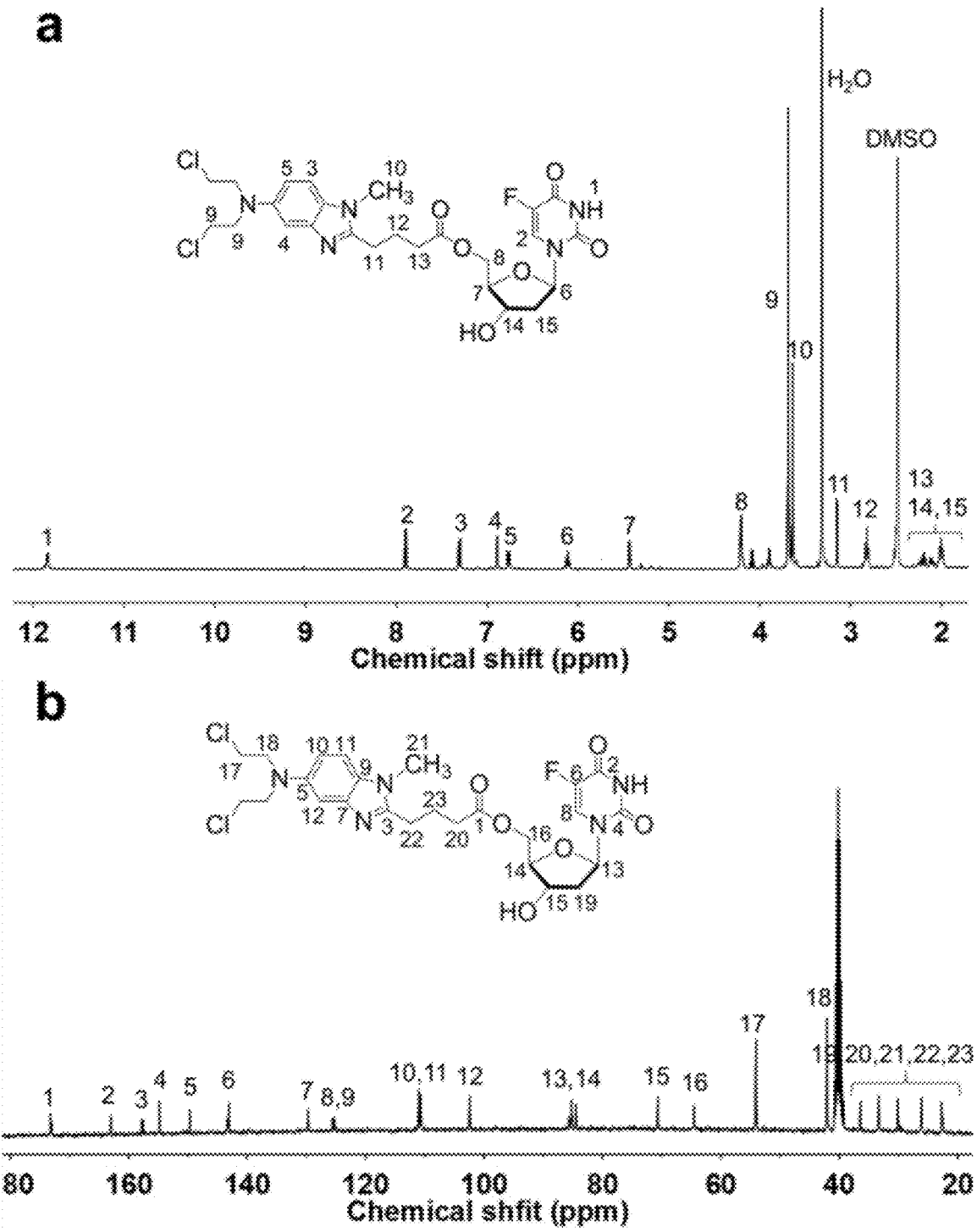
FIG. 15. Chemical characteristics of the FdU-BdM ADDC. (a) $^1$H NMR and (b) $^{13}$C NMR spectra of FdU-BdM ADDC in DMSO-d$_6$. (c) Mass spectrum of FdU-BdM ADDC.
Figure 15:
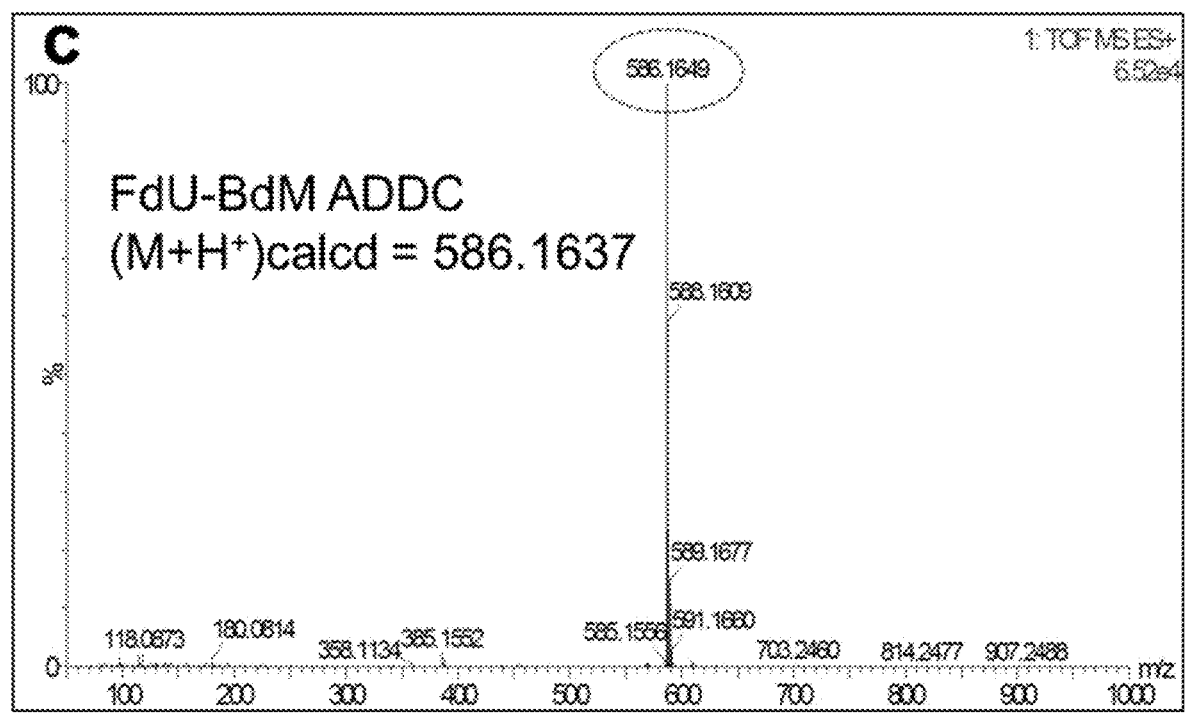
Figure 16:
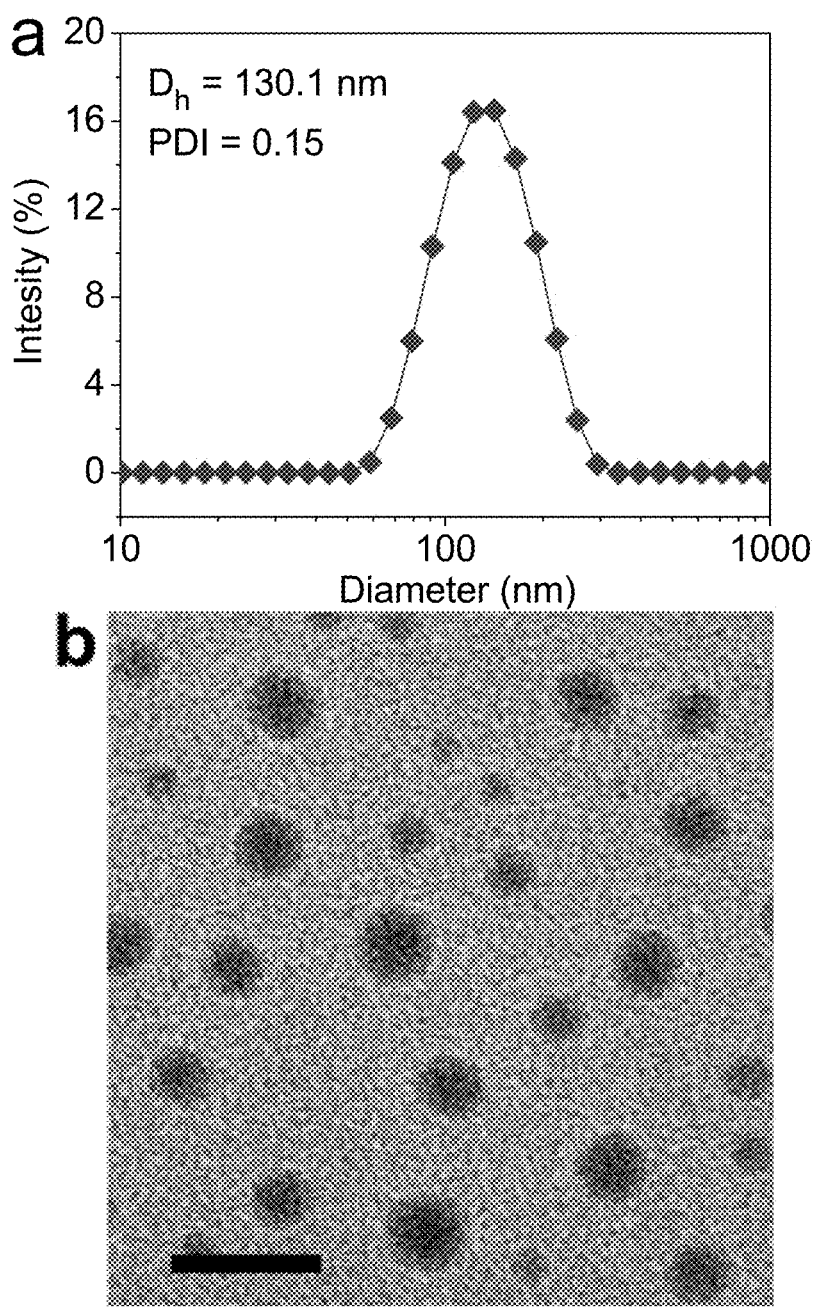
FIG. 16. Characterization of molecular self-assembly of FdU-BdM ADDC. (a) DLS curve of the FdU-BdM ADDC aqueous solution with the concentration of 0.5 mg mL$^{-1}$. (b) Representative TEM images of FdU-BdM ADDC nanoparticles (Scale bar is 200 nm).

See FIGS. 15 and 16.

Example 3

Preparation of the Gem-PAB Conjugate

PAB (88 mg, 0.2 mmol), DCC (80 mg, 0.4 mmol) and DMAP (24.2 mg, 0.2 mmol) were dissolved in dried DCM (5 mL) and the mixture was stirred at room temperature for 30 min. Then the Gem.HCl (120 mg, 0.4 mmol) in anhydrous DMF (10 mL) was added and the reaction mixture was stirred overnight at room temperature. The reaction was quenched by adding water and then the reaction mixture was extracted with ethyl acetate (EtOAc). The organic phase was collected and washed with brine (2×3 mL), dried with anhydrous $Na_2SO_4$. Then the product was purified by column chromatography to give the Gem-PAB conjugate (142 mg, 30.5%). $^1H$ NMR (400 MHz, $CDCl_3$) δ (ppm): 8.16 (d, J=7.5, 1H), 7.44 (d, J=6.5, 1H), 7.19 (s, 1H), 7.04 (d, J=11.1, 1H), 6.51 (dd, $J_1$=14.9, $J_2$=11.1, 1H), 6.22 (s, 1H), 5.77 (d, J=15.1, 1H), 4.30-4.50 (m, 2H), 4.06 (dd, J=8.4, 1H), 3.91 (dd, J=11.0, 1H), 3.72 (s, 3H), 3.32 (s, 1H), 3.07 (d, J=7.5, 1H), 2.88 (d, J=9.1, 1H), 2.74 (m, 1H), 2.61 (m, 1H), 2.13 (s, 3H), 2.12 (m, 1H), 1.99 (s, 3H), 1.69-1.82 (m, 5H), 1.58 (s, 3H). $^{13}C$ NMR (100 MHz, $CDCl_3$) δ (ppm): 173.20, 169.61, 168.20, 168.10, 163.08, 155.45, 145.10, 141.76, 136.11, 134.46, 130.51, 122.44, 121.22, 97.69, 97.55, 90.01, 83.97, 81.45, 68.93, 59.60, 55.24, 52.11, 49.14, 33.31, 30.68, 28.27, 27.68, 24.31, 21.81, 21.09, 20.09, 12.87. ESI-MS m/z ($M+Na^+$) calcd: 700.2294, found: 700.2301.

Synthesis of the Gem-PAB ADDC

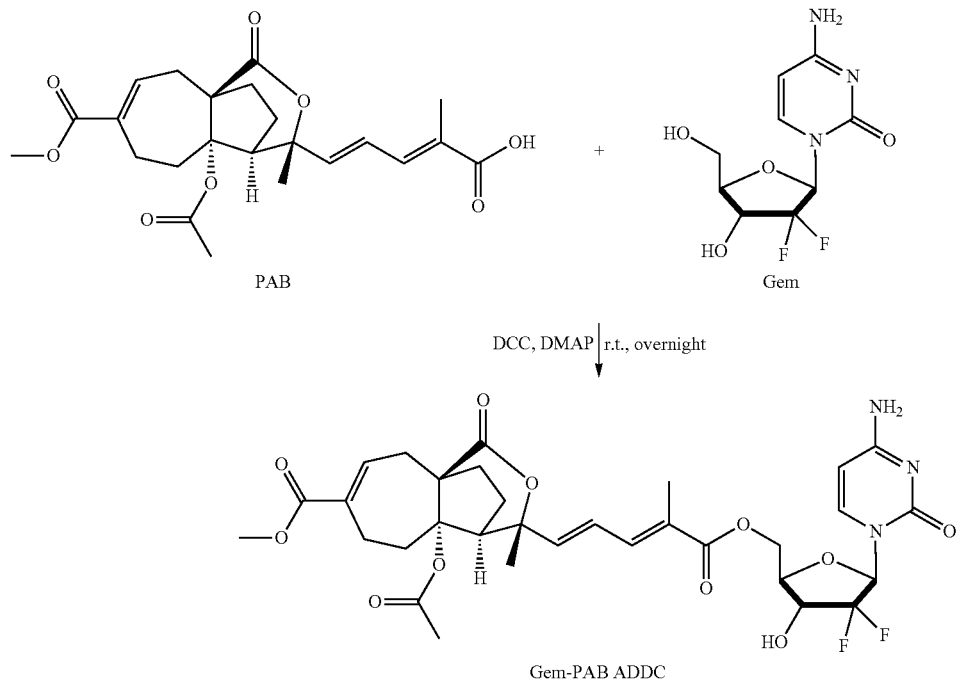

Preparation of Gem-PAB ADDC Nanoparticles

Briefly, 2 mg protonated Gem-PAB ADDC was dissolved in 2 mL of DMSO and stirred at room temperature for 5 min. Then the solution was added to 3 mL of deionized water by using a micro-syringe pump at a speed of 2 mL h$^{-1}$. Subsequently, the solution was dialyzed against deionized water for 24 h (molecular weight cutoff=1,000 g mol$^{-1}$), during which the water was renewed every 3 h and the final concentration of nanoparticles was 0.1 mg mL$^{-1}$.

Figure 17:
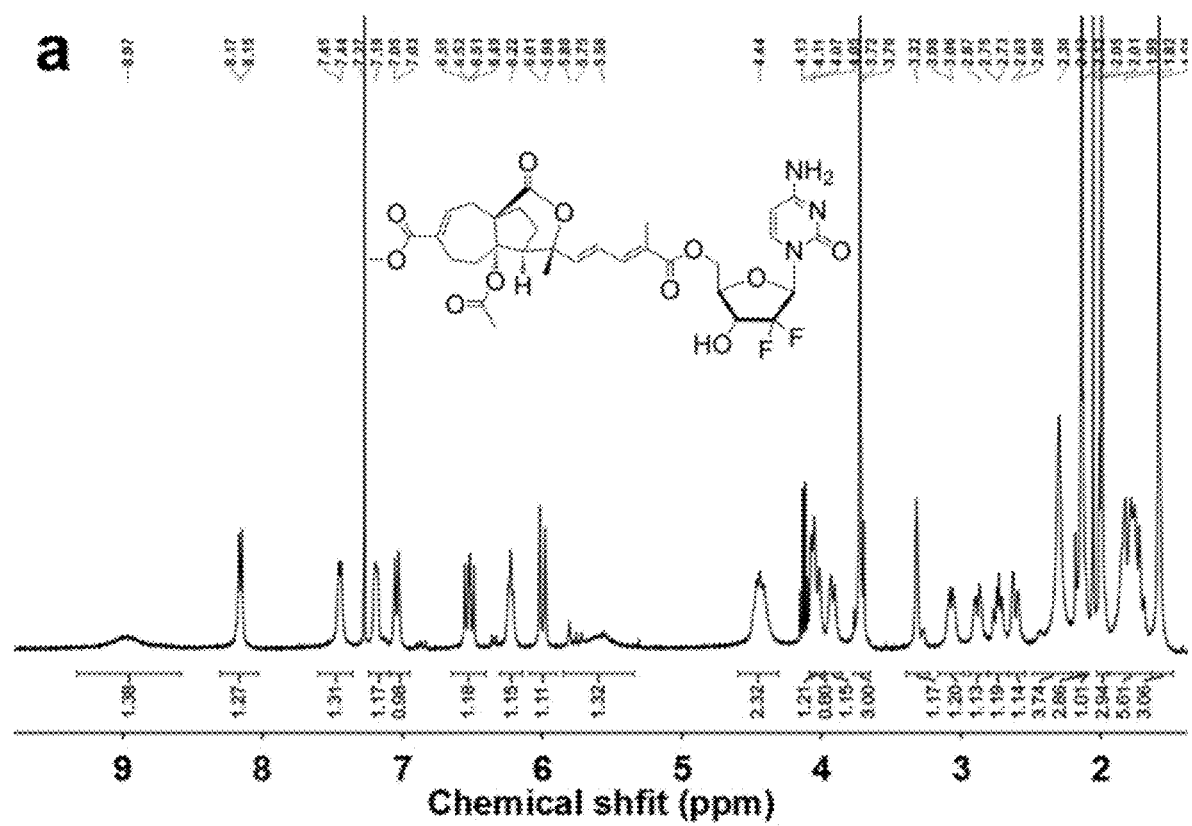
FIG. 17. Chemical characteristics of the Gem-PAB ADDC. (a) $^1$H NMR and (b) $^{13}$C NMR spectra of Gem-PAB ADDC in CDCl$_3$. (c) Mass spectrum of Gem-PAB ADDC.
Figure 17:
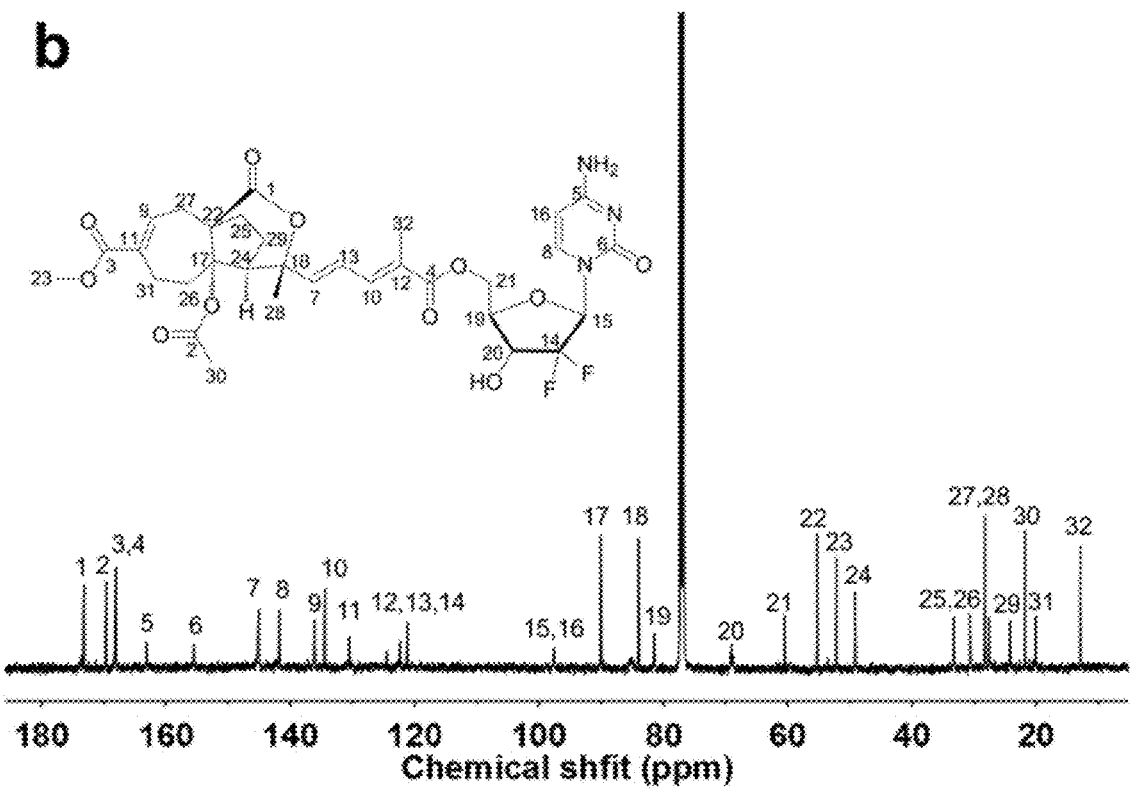
Figure 17:
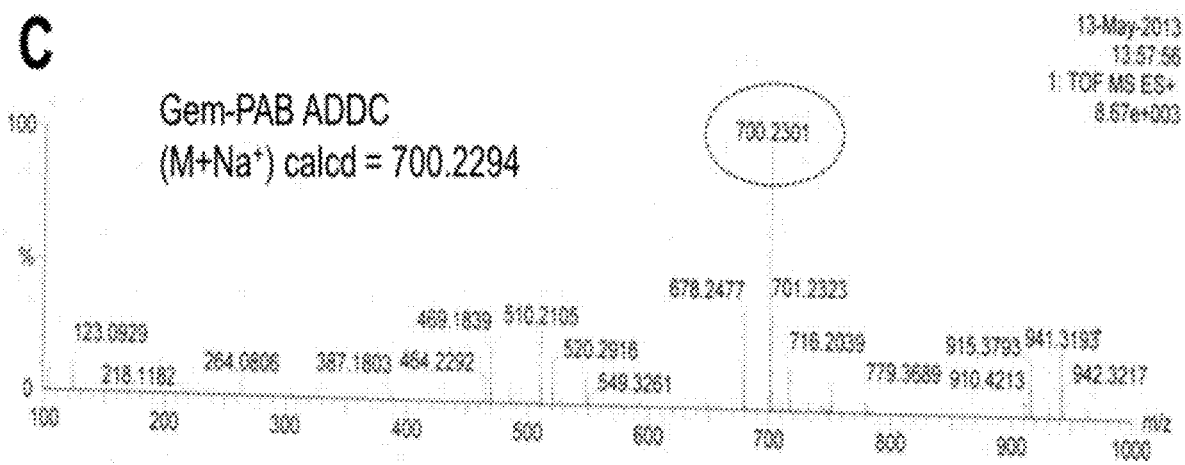
Figure 18:
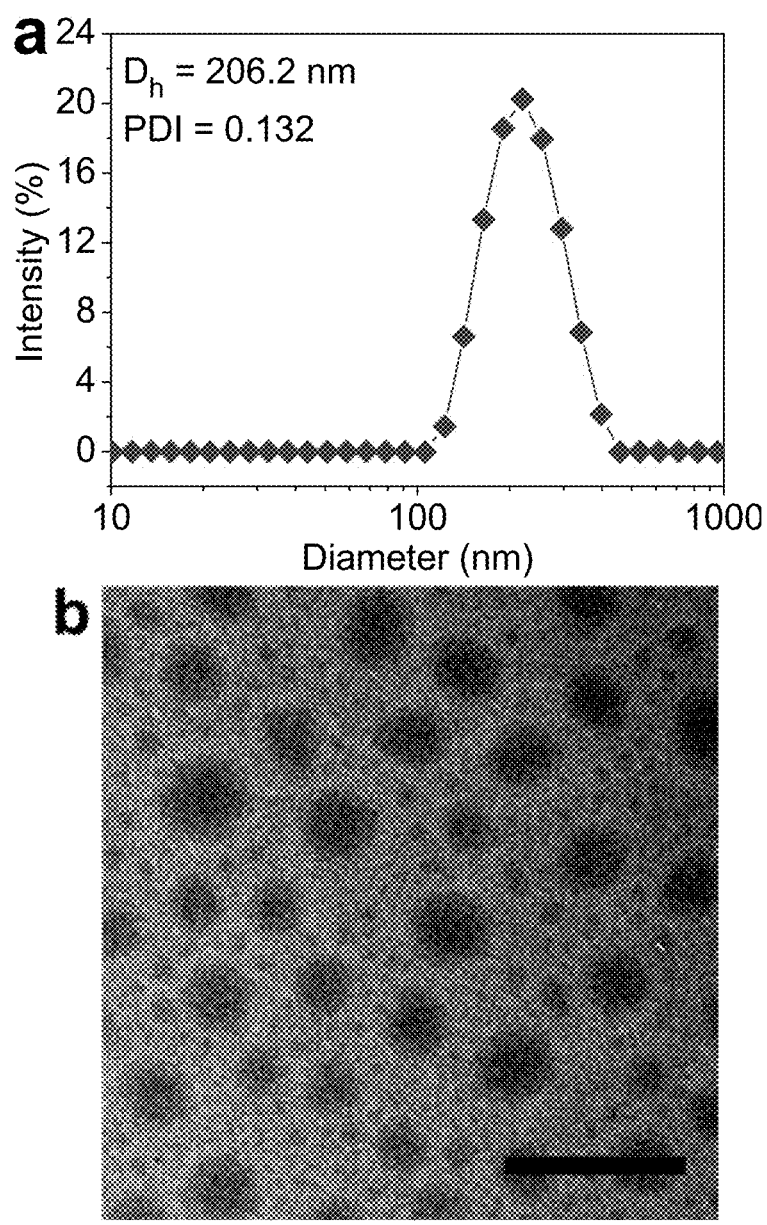
FIG. 18. Characterization of molecular self-assembly of Gem-PAB ADDC. (a) DLS curve of the Gem-PAB ADDC aqueous solution with the concentration of 0.1 mg mL$^{-1}$. (b) Representative TEM images of Gem-PAB ADDC nanoparticles (Scale bar is 500 nm).

See FIGS. 17 and 18.

Example 4

Preparation of Gem-Cb ADDC

Synthetic of Gem-Cb ADDC

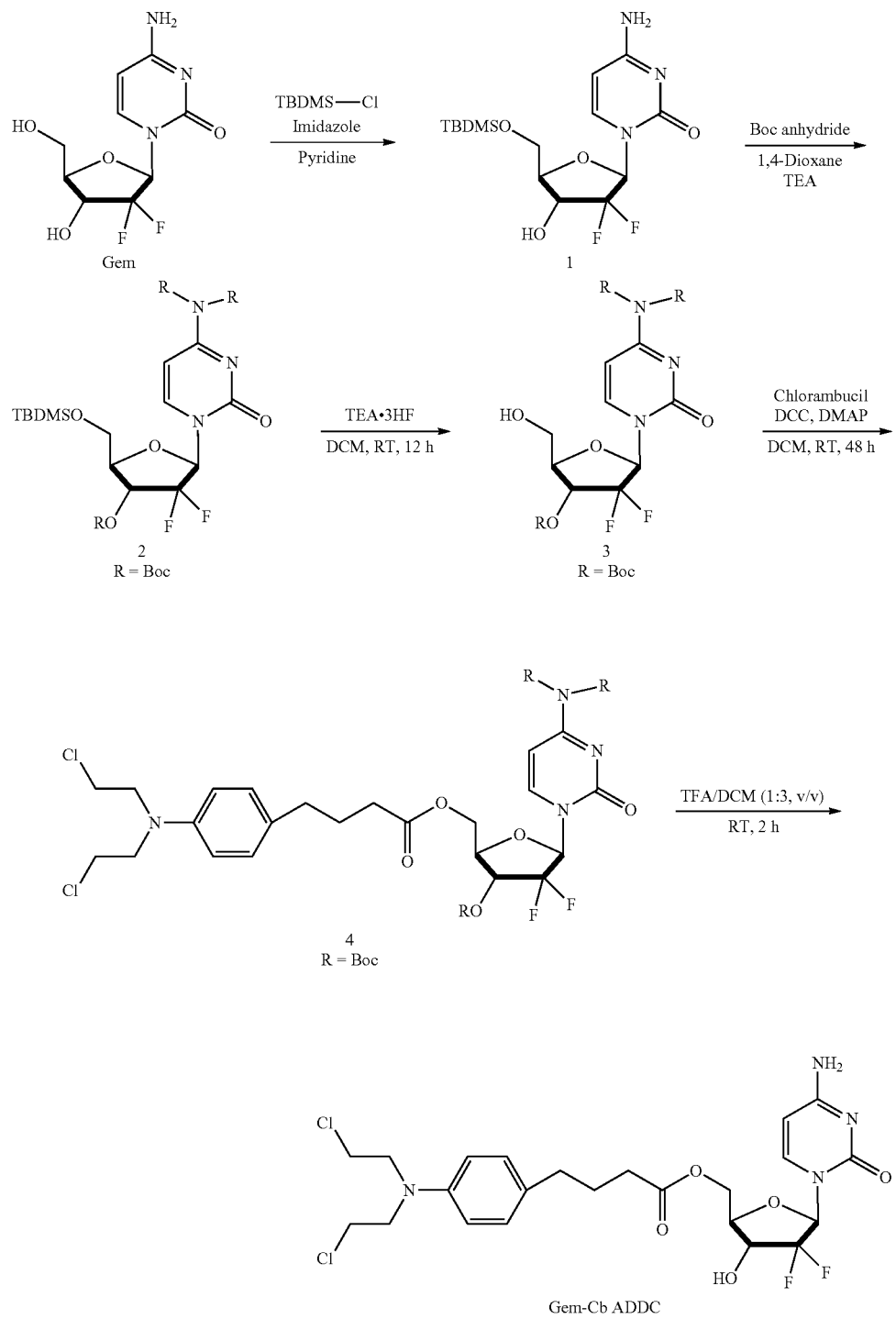

5'-O-(Tert-butyl-dimethylsilyl)-2',2'-difluoro-cytidine (1)

TBDMS-Cl (5.43 g, 36 mmol) in anhydrous pyridine (20 mL) was added to a stirred suspension of gemcitabine hydrochloride (Gem.HCl) (7.90 g, 30 mmol) and imidazole (2.45 g, 36 mmol) in anhydrous pyridine (60 mL). The reaction mixture was stirred at room temperature for 3 h and then the solvent was removed under reduced pressure. The residue was dissolved in 200 mL EtOAc, and washed with water (2×20 mL), dried over anhydrous $Na_2SO_4$. After filtration and evaporation to dryness, the crude product was purified by using recrystallization from EtOAc to give 1 (4.95 g, 43.7%). $^1$H NMR (400 MHz, DMSO-$d_6$) δ (ppm): 7.62 (d, J=7.5 Hz, 1H), 7.41 (d, J=12.3 Hz, 2H), 6.31 (d, J=6.5 Hz, 1H), 6.12 (t, J=7.7 Hz, 1H), 5.74 (d, J=7.5 Hz, 1H), 4.10 (m, 1H), 3.92 (d, J=11.6 Hz, 1H), 3.85-3.77 (m, 3H), 0.86 (s, 9H, C(CH$_3$)$_3$), 0.06 (s, 6H, Si(CH$_3$)$_2$). $^{13}$C NMR (100 MHz, DMSO-$d_6$) δ (ppm) 166.25, 155.26, 140.53, 123.62, 95.22, 84.42, 80.39, 69.03, 61.34, 40.76, 26.39, 18.67, −4.90.

4-N,N-3'-O-Tris-(tert-butyloxycarbonyl)-5'-O-(tert-Butyl-dimethylsilyl)-2',2'-difluoro-cytidine (2)

A stirred solution of 1 (4.01 g, 10.62 mmol), DMAP (0.17 g, 1.38 mmol) and TEA (40 mL) in 1,4-dioxane (20 mL), Boc (23.18 g, 106.2 mmol) in 1,4-dioxane (50 mL) was added dropwise at 0° C. and stirred at room temperature for 19 h. Solvents were evaporated under reduced pressure. The crude product was purified by flash column chromatograph over silica gel with EtOAc/petroleum ether (1:5, v/v) to give 2 (4.69 g, 65.2%). $^1$H NMR (400 MHz, DMSO-$d_6$) δ (ppm): 8.10 (d, J=7.7 Hz, 1H), 6.98 (d, J=7.7 Hz, 1H), 6.29 (t, J=8.1 Hz, 16H), 5.29-5.15 (m, 1H), 4.37-4.27 (m, 1H), 4.02-3.84 (m, 2H), 1.47 (s, 18H, C(CH$_3$)$_3$, Boc), 1.44 (s, 9H, C(CH$_3$)$_3$, Boc), 0.86 (s, 9H, C(CH$_3$)$_3$), 0.067 (d, J=3.7 Hz, 6H, Si(CH$_3$)$_2$). $^{13}$C NMR (100 MHz, DMSO-$d_6$) δ (ppm): 163.05, 153.40, 151.84, 149.53, 145.63, 141.85, 122.11, 96.69, 85.69, 84.53, 79.14, 72.97, 61.73, 55.56, 27.85, 27.72, 27.72, 26.27, 18.55, −5.88.

4-N,N-3'-O-Tris-(tert-butyloxycarbonyl)-2',2'-difluoro-cytidine (3)

To a solution of 2 (2.37 g, 3.5 mmol) in anhydrous THF (35 mL), TEA.3HF (2.82 g, 17.5 mmol) was added. The reaction mixture was stirred at room temperature for 12 h, and the reaction was monitored by TLC. The solvent was evaporated under high vacuum. EtOAc (200 mL) was added to the reaction mixture and the solution was washed with brine (2×10 mL) and water (1×10 mL), dried over $Na_2SO_4$, and concentrated to dryness under reduced pressure. The residue was subjected to flash column chromatograph over silica gel with EtOAc/petroleum ether (1:1, v/v) to give 3 (1.32 g, 67.1%). $^1$H NMR (400 MHz, DMSO-$d_6$) δ (ppm): 8.23 (d, J=7.7 Hz, 1H), 6.94 (d, J=7.6 Hz, 1H), 6.27 (t, J=8.4 Hz, 1H), 5.34 (s, 1H), 5.24-5.15 (m, 1H), 4.25 (t, J=6.9, 3.3 Hz, 1H), 3.77 (d, J=10.6 Hz, 1H), 3.66 (d, J=9.6 Hz, 1H), 1.47 (s, 18H, C(CH$_3$)$_3$, Boc), 1.42 (s, 9H, C(CH$_3$)$_3$, Boc). $^{13}$C NMR (100 MHz, DMSO-$d_6$) δ (ppm): 162.90, 153.51, 151.90, 149.59, 146.48, 122.13, 96.82, 85.69, 84.45, 79.83, 73.04, 59.72, 55.57, 27.81, 27.19.

Synthesis of Boc-Protected Gem-Cb Conjugate (4)

A reaction mixture of 3 (1.00 g 1.77 mmol), Cb (1.10 g, 3.61 mmol), DCC (0.88 g, 4.20 mmol), DMAP (0.22 g, 1.77 mmol) in DCM (80 mL) was stirred at room temperature for 48 h. The reaction level was monitored by TLC EtOAc/petroleum ether (1:1, v/v). After 48 h, the reaction mixture was filtered and evaporated to dryness under reduced pressure. The product was purified by flash column chromatograph over silica gel with EtOAc/petroleum ether (1:5, v/v) to give 4 (0.77 g, 51.1%). $^1$H NMR (400 MHz, DMSO-$d_6$) δ (ppm): 8.10 (d, J=7.7 Hz, 1H), 6.98 (dd, J=8.6, 7.7 Hz, 2H), 6.63 (d, J=8.7 Hz, 1H), 6.29 (t, J=8.7 Hz, 1H), 4.57-4.27 (m, 4H, H5, H7), 3.66 (s, 8H), 2.43 (d, J=7.7 Hz, 2H), 2.32 (t, J=7.4 Hz, 2H), 1.73 (m, 2H), 1.48 (s, 18H, C(CH$_3$)$_3$, Boc), 1.43 (s, 9H, C(CH$_3$)$_3$, Boc). $^{13}$C NMR (100 MHz, DMSO-$d_6$) δ (ppm): 173.15, 162.97, 153.43, 151.78, 149.56, 147.04, 145.13, 130.02, 121.92, 112.53, 96.89, 85.73, 84.55, 76.82, 73.74, 62.93, 52.90, 41.76, 33.88, 33.33, 27.81, 27.76, 27.08.

Synthesis of Gem-Cb ADDC

The Boc-protected Gem-Cb conjugate 4 (0.70 g, 0.82 mmol) was dissolved in anhydrous DCM (25 mL), and TFA (10 mL) was added dropwise at 0° C. and the solution was stirred for 2 h. The solvent was evaporated under high vacuum. The residue was dissolved in DCM (100 mL) and washed with saturated $NaHCO_3$ (2×10 mL) and brine (1×10 mL), dried over anhydrous $Na_2SO_4$, and concentrated to dryness to give the Gem-Cb conjugate (0.34 g, 75.0%). $^1$H NMR (400 MHz, DMSO-$d_6$) δ (ppm): 7.49 (d, J=7.5 Hz, 1H), 7.39 (s, 1H), 7.02 (d, J=8.6 Hz, 2H), 6.64 (d, J=6.4 Hz, 2H), 6.40 (d, J=6.4 Hz, 1H), 6.15 (t, J=7.7 Hz, 1H), 4.42-4.19 (m, 2H), 4.24-4.01 (s, 1H), 4.01-3.95 (m, 1H), 3.67 (s, 8H), 2.44 (d, J=7.3 Hz, 2H), 2.32 (t, J=7.3 Hz, 2H), 1.75 (m, 2H). $^{13}$C NMR (100 MHz, DMSO-$d_6$) δ (ppm): 173.23, 166.30, 155.21, 145.14, 141.85, 130.03, 129.68, 125.91, 123.34, 112.54, 95.58, 78.02, 71.05, 63.27, 52.90, 41.82, 33.90, 33.40, 27.17. ESI-MS m/z (M+H$^+$) calcd: 549.1424, found: 549.1472.

Preparation of Gem-Cb ADDC Nanoparticles

The Gem-Cb nanoparticles were prepared by a dialysis method. 2 mg Gem-Cb ADDC was dissolved in 20 mL of 1,4-dioxane. Then 1 mL of the Gem-Cb 1,4-dioxane solution was added dropwise into 2.5 mL of ultrapure water by using a micro-syringe pump. Subsequently, the solution was transferred into a dialysis bag (molecular weight cutoff=1000 g mol$^{-1}$) and dialyzed against deionized water for 24 h.

Figure 19:
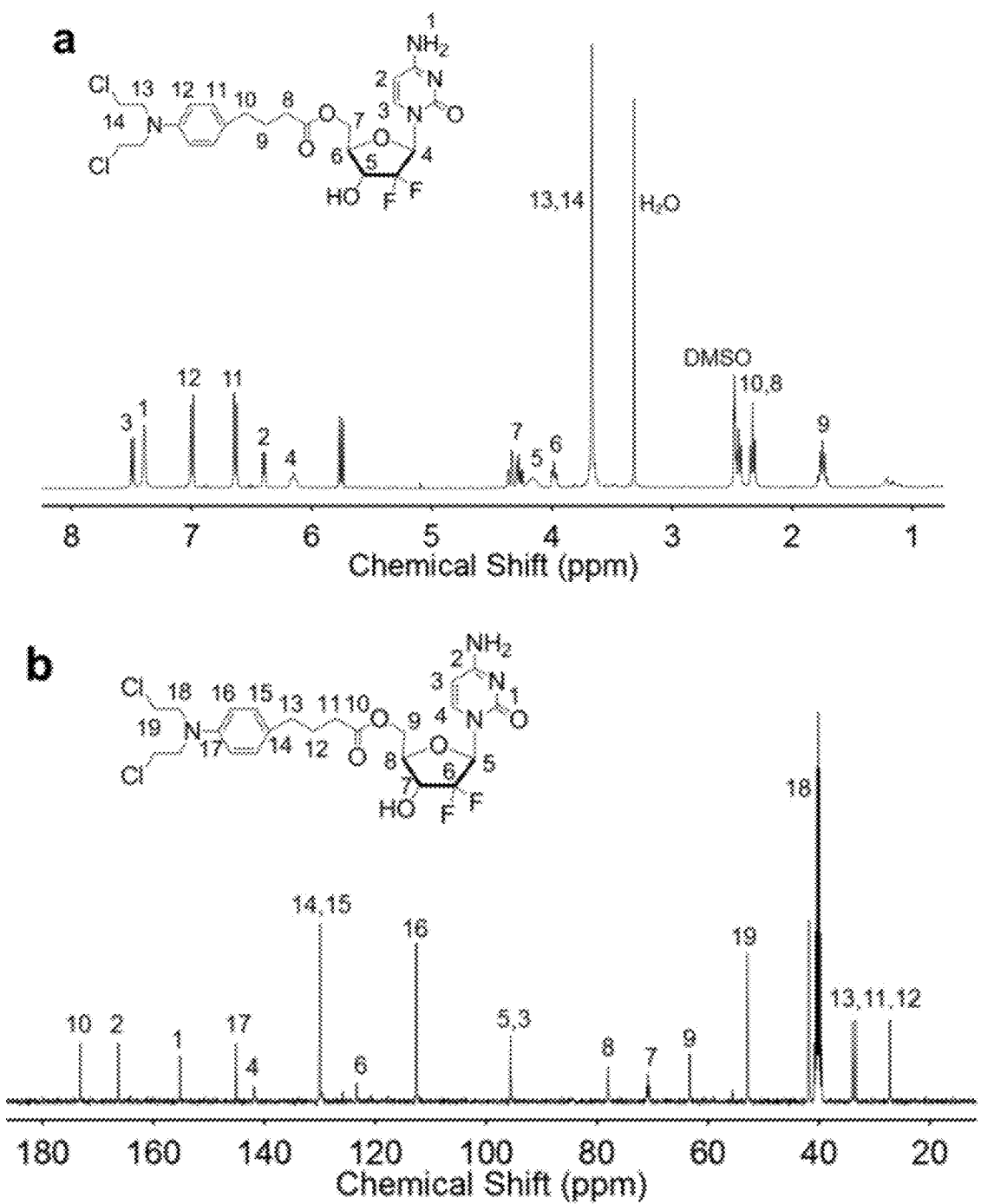
FIG. 19. Chemical characteristics of the Gem-Cb ADDC. (a) $^1$H NMR and (b) $^{13}$C NMR spectra of Gem-Cb ADDC in DMSO-d$_6$. (c) Mass spectrum of Gem-Cb ADDC.
Figure 19:
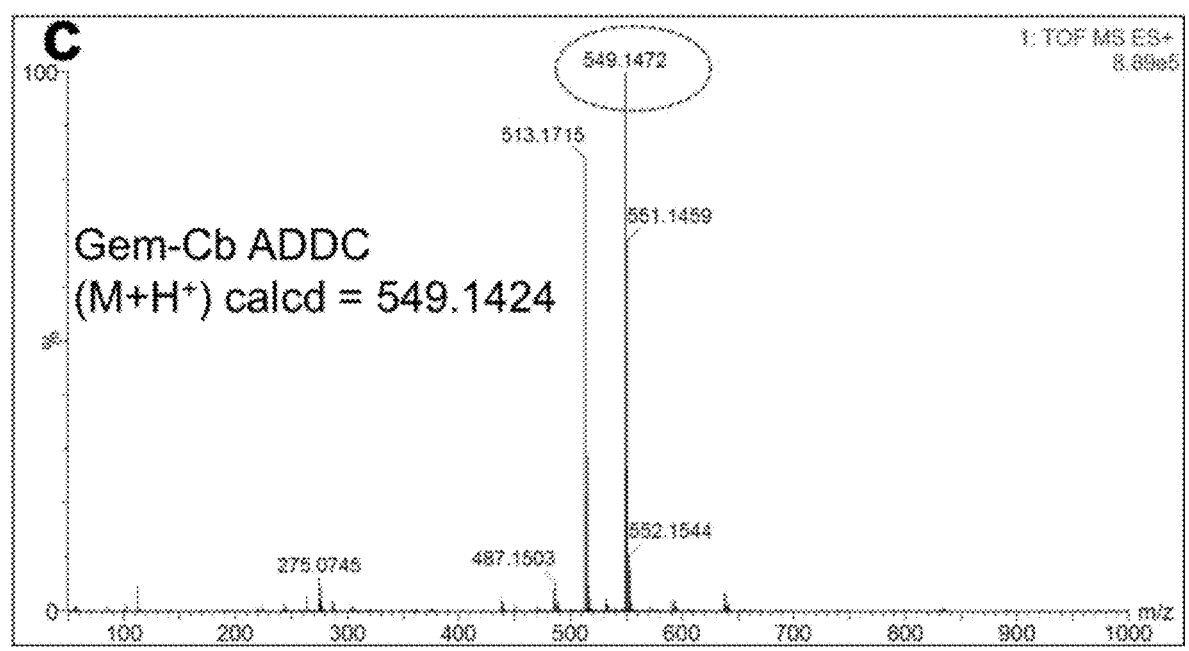
Figure 20:
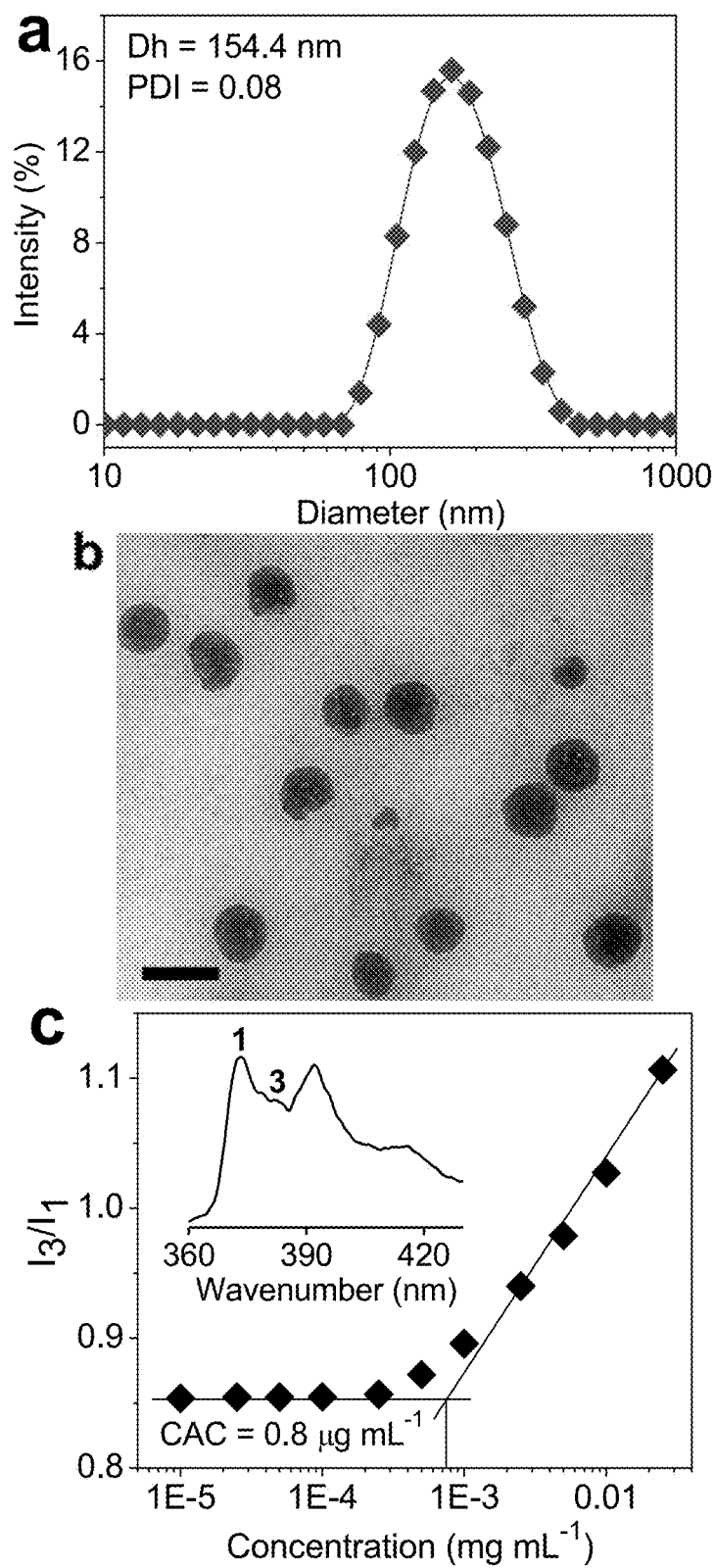
FIG. 20. Characterization of molecular self-assembly of Gem-Cb ADDC. (a) DLS curve of the Gem-Cb ADDC aqueous solution with the concentration of 0.2 mg mL$^{-1}$. (b) Representative TEM images of Gem-Cb ADDC nanoparticles (Scale bar is 200 nm). (c) Relationship between the fluorescent intensity ratio (I$_3$/I$_1$) and Gem-Cb ADDC concentration in water (Inset: the fluorescence emission spectrum of pyrene in aqueous solution).
Figure 21:
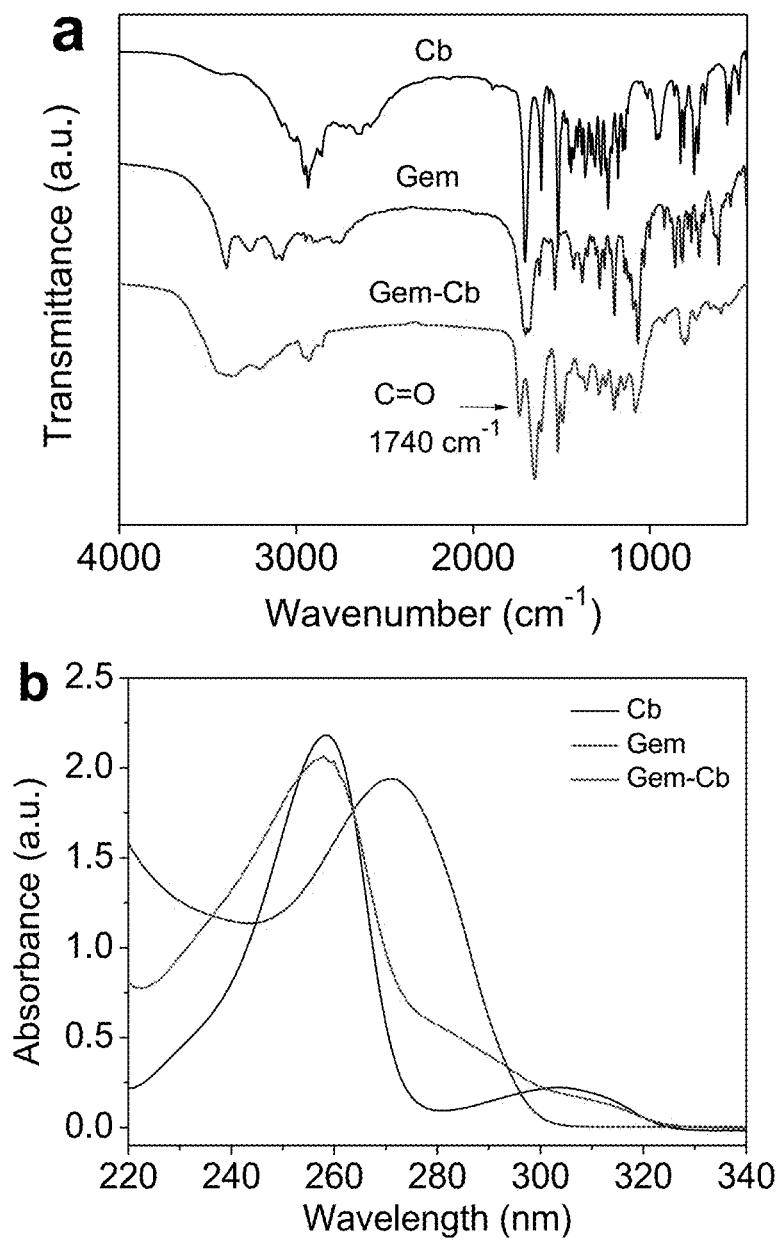
FIG. 21. Spectroscopic analysis of Gem-Cb conjugate. (a) FITR spectra of Cb, Gem and Gem-Cb conjugate. (b) UV/Vis spectra of Cb, Gem and Gem-Cb conjugate.

See FIGS. 19, 20 and 21.

Example 5

Preparation of Gem-MTX ADDC

The Gem-MTX ADDC was synthesized used the same methods with example 3. In a typical procedure, a reaction mixture of 3 in example 3 (1.13 g, 2 mmol), MTX (0.90 g, 2 mmol), DCC (0.83 g, 4 mmol), DMAP (0.25 g, 2 mmol) in DCM (80 mL) was stirred at room temperature for 48 h. The reaction level was monitored by TLC DCM/CH$_3$OH (10:1, v/v). After 48 h, the reaction mixture was filtered and evaporated to dryness under reduced pressure. The product was purified by flash column chromatograph over silica gel with DCM/CH$_3$OH (10:1, v/v) to give 5 (0.77 g, 51.1%).

Synthesis of Gem-MTX ADDC

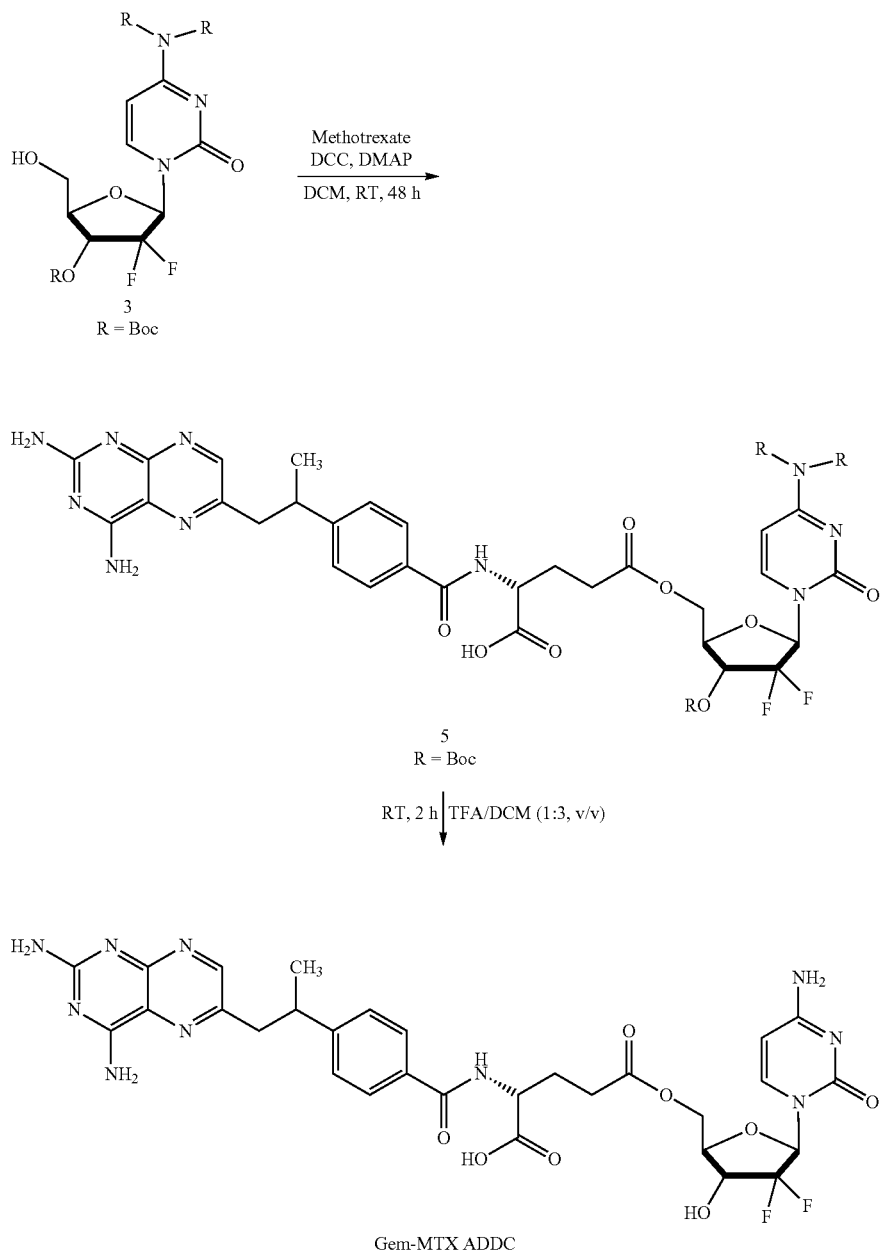

To a stirred solution of 5 (0.70 g, 0.82 mmol) in anhydrous DCM (25 mL) was added TFA (10 mL) dropwise at 0° C. and the mixture was stirred for 2 h. Then the solvent was evaporated under high vacuum. The residue was purified by flash column chromatograph over silica gel with DCM/CH$_3$OH (2:1, v/v) to give the compound Gem-MTX conjugate (0.34 g, 75.0%). $^1$H NMR (400 MHz, DMSO-d$_6$) δ (ppm): 11.16 (s, 1H), 9.11 (s, 1H), 8.54 (s, 1H), 8.25-8.23 (dd, J=7.6 Hz, 1H), 7.74-7.72 (d, J=8.8 Hz, 1H), 7.64 (s, 2H), 6.81-6.79 (d, J=8.8 Hz, 1H), 6.59 (s, 2H), 6.17-6.13 (t, J=8.8 Hz, 1H), 4.76 (s, 2H), 4.41 (m, 1H), 4.18-4.16 (t, J=8 Hz, 1H), 3.87-3.85 (m, 1H), 3.79-3.76 (d, J=12 Hz, 1H), 3.64-3.62 (m, J=10.4 Hz, 1H), 3.18 (s, 3H), 2.22-2.20 (t, J=6 Hz, 2H), 1.94-1.93 (t, J=6.8 Hz, 2H). $^{13}$C NMR (100 MHz, DMSO-d$_6$) δ (ppm): 174.83, 173.16, 167.59, 164.78, 161.10, 160.93, 158.06, 155.43, 152.74, 151.96, 144.78, 142.76, 136.81, 130.09, 128.24, 126.79, 121.37, 95.62, 69.17, 68.35, 62.25, 56.98, 44.32, 36.34, 30.52, 26.19, 17.43. ESI-MS m/z (M−H$^+$) calcd: 698.2302, found: 698.2197.

Preparation of Gem-MTX ADDC Nanoparticles

Typically, 5 mg Gem-MTX ADDC was dissolved in 2 mL of DMF and stirred at room temperature for 20 min. Then the DMF was removed by rotary evaporation. Subsequently, 50 mL of ultrapure water was added and the solution was ultrasonicated at room temperature for 30 min.

Figure 22:
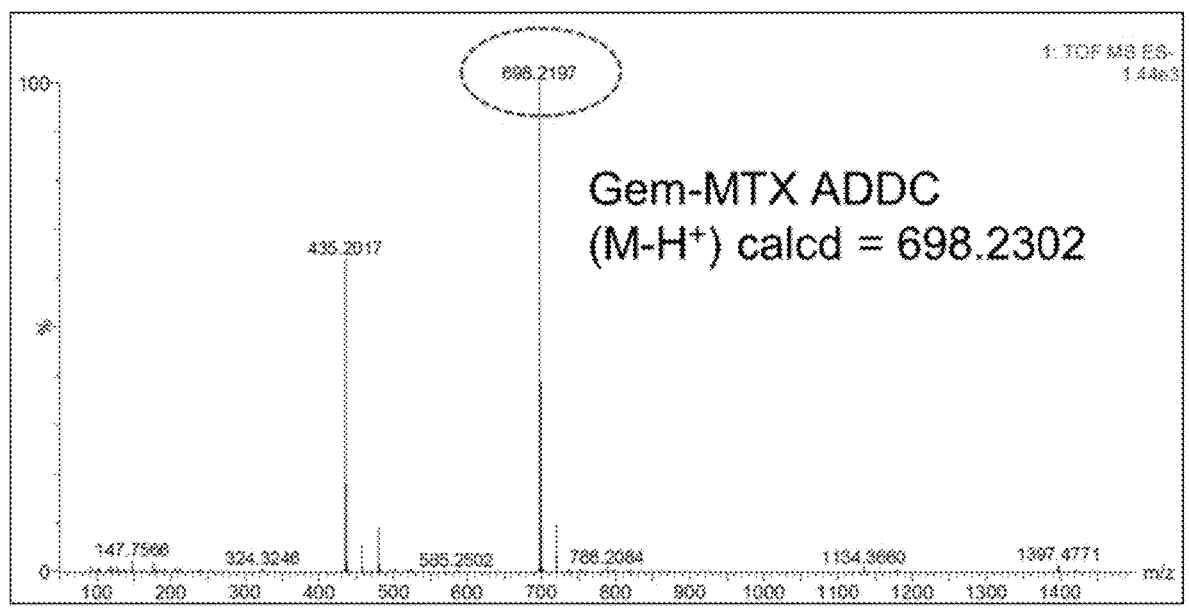
FIG. 22. Mass spectrum of Gem-MTX ADDC.
Figure 23:
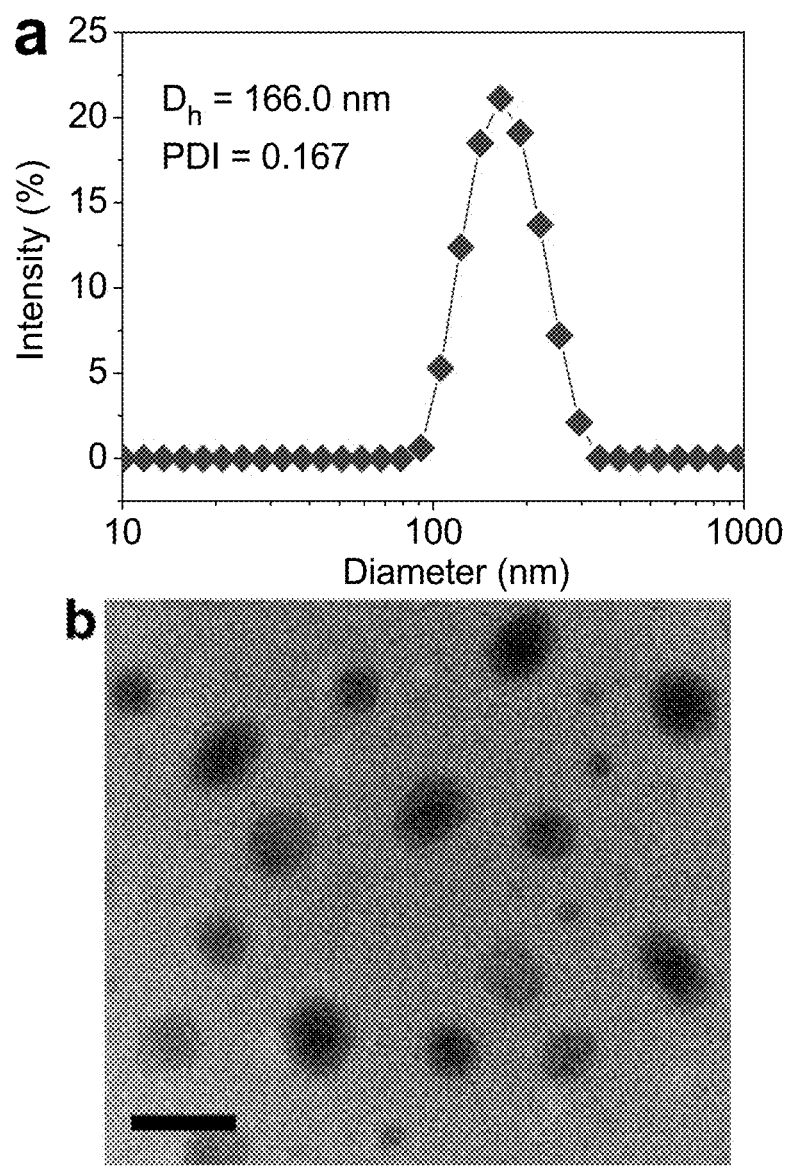
FIG. 23. Characterization of molecular self-assembly of Gem-MTX ADDC. (a) DLS curve of the Gem-MTX ADDC aqueous solution with the concentration of 0.1 mg mL$^{-1}$. (b) Representative TEM images of Gem-MTX ADDC nanoparticles (Scale bar is 200 nm).

See FIGS. 22, and 23.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A method of treating cancer, comprising administering to a subject in need thereof a composition comprising a therapeutically effective amount of a compound selected from the group consisting of:

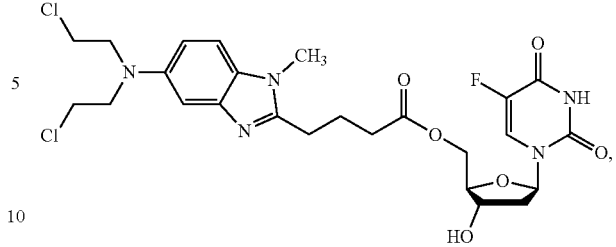

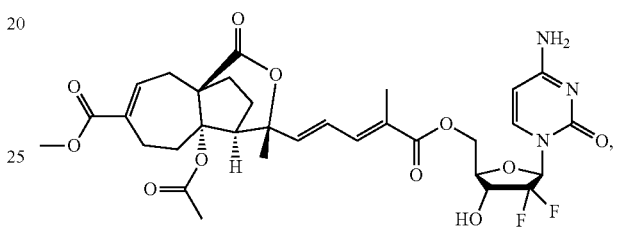

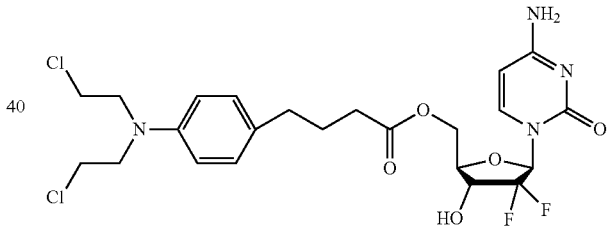

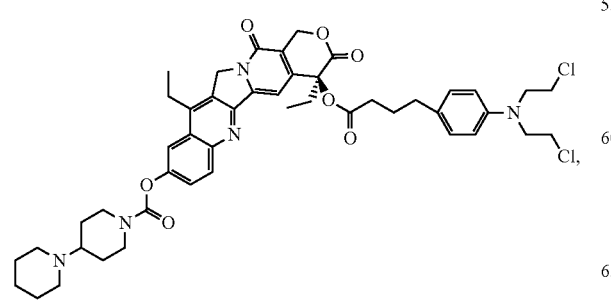

and

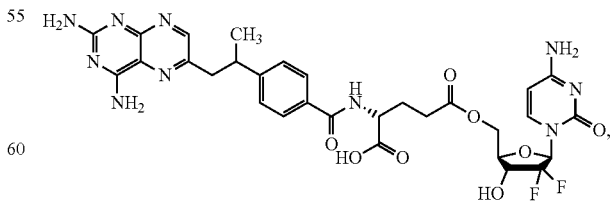

or a derivative amphiphilic conjugate thereof.

2. The method of claim 1, wherein the compound has the structural formula:

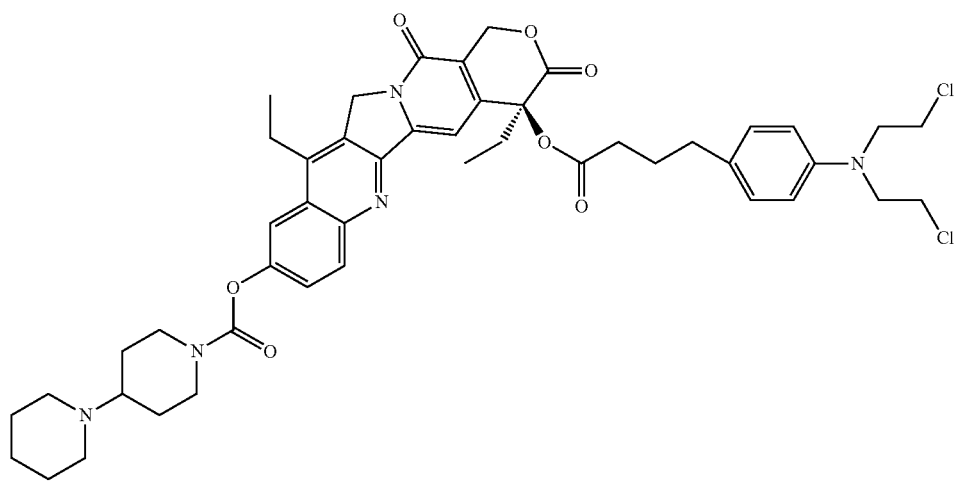 [SMILES: CCc1c2c(nc3ccc(OC(=O)N4CCC(N5CCCCC5)CC4)cc13)-c1cc3c(c(=O)n1C2)COC(=O)[C@@]3(CC)OC(=O)CCCc1ccc(N(CCCl)CCCl)cc1]
or a derivative amphiphilic conjugate thereof.
3. The method of claim 1, wherein the compound has the structural formula:
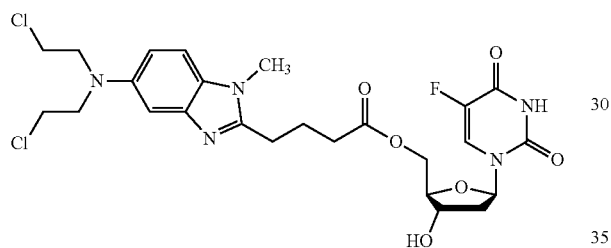
or a derivative amphiphilic conjugate thereof.
4. The method of claim 1, wherein the compound has the structural formula:
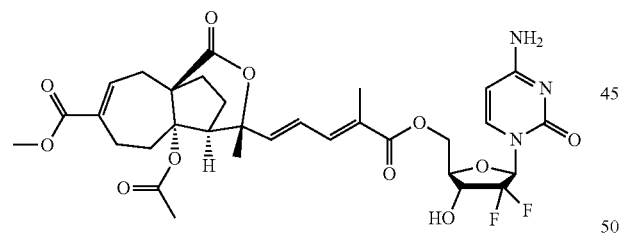
or a derivative amphiphilic conjugate thereof.
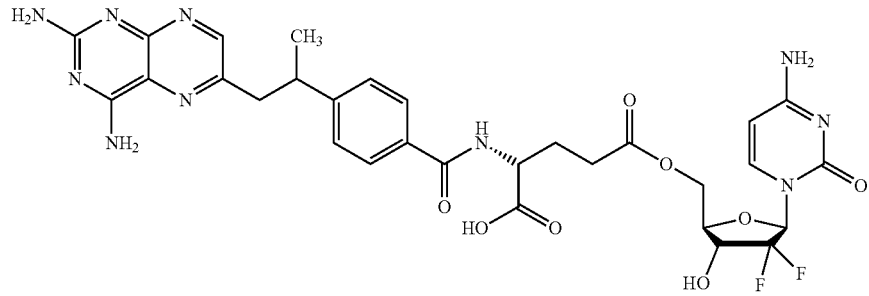

5. The method of claim 1, wherein the compound has the structural formula:
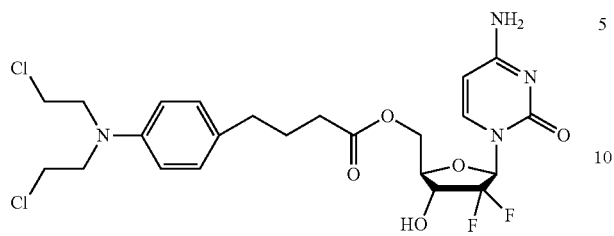
or a derivative amphiphilic conjugate thereof.
6. The method of claim 1, wherein the compound has the structural formula:
or a derivative amphiphilic conjugate thereof.
7. The method of claim 1, wherein the compound is present in the form of a nanoparticle.
* * * * *